US008461153B2

(12) United States Patent
Glick

(10) Patent No.: US 8,461,153 B2
(45) Date of Patent: Jun. 11, 2013

(54) BENZODIAZEPINONE COMPOUNDS USEFUL IN THE TREATMENT OF SKIN CONDITIONS

(75) Inventor: Gary D. Glick, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 13/283,231

(22) Filed: Oct. 27, 2011

(65) Prior Publication Data

US 2012/0040971 A1 Feb. 16, 2012

Related U.S. Application Data

(63) Continuation of application No. 12/266,239, filed on Nov. 6, 2008.

(60) Provisional application No. 60/985,898, filed on Nov. 6, 2007.

(51) Int. Cl.
- *C07D 243/18* (2006.01)
- *A61K 31/55* (2006.01)
- *A61P 17/00* (2006.01)
- *A61P 17/06* (2006.01)

(52) U.S. Cl.
USPC .......................................... 514/221; 540/504

(58) Field of Classification Search
USPC .......................................... 540/504; 514/221
See application file for complete search history.

(56) References Cited

U.S. PATENT DOCUMENTS

| | | | |
|---|---|---|---|
| 3,261,828 A | 7/1966 | Uskokovic | |
| 3,374,264 A | 3/1968 | Uskokovic | |
| 3,384,635 A | 5/1968 | Calabateas | |
| 3,415,814 A | 12/1968 | Calabeteas | |
| 3,847,905 A | 11/1974 | Bub | |
| 4,076,823 A | 2/1978 | Wade | |
| 4,088,756 A | 5/1978 | Voorhees | |
| 4,108,852 A | 8/1978 | Bub | |
| 4,110,337 A | 8/1978 | Szarvasi | |
| RE30,293 E | 6/1980 | Bub | |
| 4,495,101 A | 1/1985 | Klaubert | |
| 4,551,480 A | 11/1985 | Stiefel | |
| 4,560,684 A | 12/1985 | Sugasawa | |
| 4,623,646 A | 11/1986 | Casals-Stenzel | |
| 4,751,223 A | 6/1988 | Glarnkowski | |
| 4,820,834 A | 4/1989 | Evans | |
| 4,894,366 A | 1/1990 | Okuhara | |
| 4,898,861 A | 2/1990 | Morgan | |
| 4,916,138 A | 4/1990 | Ueda | |
| 4,929,611 A | 5/1990 | Okuhara | |
| 4,946,778 A | 8/1990 | Ladner | |
| 5,004,741 A | 4/1991 | Evans | |
| 5,041,438 A | 8/1991 | Hsu | |
| 5,141,930 A | 8/1992 | Nakao | |
| 5,147,872 A | 9/1992 | Golwyn | |
| 5,216,148 A | 6/1993 | Klaus | |
| 5,288,514 A | 2/1994 | Ellman | |
| 5,324,726 A | 6/1994 | Bock | |
| 5,391,566 A | 2/1995 | Chakravarty | |
| 5,444,092 A | 8/1995 | Collins | |
| 5,521,170 A | 5/1996 | Setoi | |
| 5,545,568 A | 8/1996 | Ellman | |
| 5,559,230 A | 9/1996 | Ogawa | |
| 5,591,227 A | 1/1997 | Dihn | |
| 5,597,915 A | 1/1997 | Chambers | |
| 5,599,352 A | 2/1997 | Dihn | |
| 5,633,251 A | 5/1997 | Claremon | |
| 5,677,282 A | 10/1997 | Oleksyszyn | |
| 5,697,967 A | 12/1997 | Dihn | |
| 5,763,437 A | 6/1998 | Sato | |
| 5,776,946 A | 7/1998 | McGeer | |
| 5,861,380 A | 1/1999 | Gyorkos | |
| 5,962,337 A | 10/1999 | Ohlmeyer | |
| 6,004,942 A | 12/1999 | Firestein | |
| 6,074,859 A | 6/2000 | Hirokawa | |
| 6,080,568 A | 6/2000 | Day | |
| 6,100,254 A | 8/2000 | Budde | |
| 6,239,131 B1 | 5/2001 | Shinozaki | |
| 6,277,844 B1 | 8/2001 | Spector | |
| 6,319,931 B1 | 11/2001 | Kroemer | |
| 6,506,744 B1 | 1/2003 | Alig | |
| 6,524,623 B1 | 2/2003 | Hodosh | |
| 6,524,832 B1 | 2/2003 | Kufe | |
| 2,457,405 A1 | 3/2003 | Glick | |
| 6,579,854 B1 | 6/2003 | Mitchell | |
| 6,605,593 B1 | 8/2003 | Naicker | |
| 6,613,739 B1 | 9/2003 | Naicker | |

(Continued)

FOREIGN PATENT DOCUMENTS

| CA | 2372150 | 11/2000 |
|---|---|---|
| CA | 2457405 | 2/2003 |

(Continued)

OTHER PUBLICATIONS

Gupta et al., "Psychitripic drugs in dermatology . . . " Database:EMbase (AN:86111413), Journal of the American Academy of Dermatology, 1986, vol. 14, No. 4, pp. 633-645.
Lowe, "Systemic treatment of severe psoriasis," The New England Journal of Medicine, 324 (5), Feb. 7, 1991, pp. 333-334.
Laupacis, et al., "Cyclosporin A: a powerful immunosuppressant", CMA Journal, May 1, 1982, vol. 126, pp. 1041-1046.
Otto, M.W., et al. (2005) J. Clin. Psychiatry 66 Suppl. 2:34-38.
Yoshi, M., et al., (2005) Nippon Yakurigaku Zasshi 125(1):33-36.
Yasuda, K., (2004) Nippon Rinsho. 62 Suppl. 12:360-363.

(Continued)

*Primary Examiner* — Bruck Kifle
(74) *Attorney, Agent, or Firm* — Casimir Jones SC

(57) ABSTRACT

The present invention provides a family of benzodiazepinone compounds and pharmaceutical compositions thereof. The present invention also provides methods of treating certain skin conditions, e.g., atopic dermatitis, rosacea, or psoriasis, by administering a benzodiazepinone and methods of reducing the proliferation of keratinocyte cells by exposing such cells to a benzodiazepinone.

17 Claims, No Drawings

U.S. PATENT DOCUMENTS

| | | | |
|---|---|---|---|
| 6,767,533 B1 | 7/2004 | Casellas |
| 6,824,561 B2 | 11/2004 | Soykan |
| 6,916,813 B2 | 7/2005 | Atwal |
| 7,109,224 B2 | 9/2006 | Kempson |
| 7,125,866 B1 | 10/2006 | Glick |
| 7,144,880 B2 | 12/2006 | Glick |
| 7,150,433 B2 | 12/2006 | Healy |
| 7,175,953 B2 | 2/2007 | Licha |
| 7,220,739 B2 | 5/2007 | Glick |
| 7,250,410 B2 | 7/2007 | Bourguignon |
| 7,276,348 B2 | 10/2007 | Glick |
| 7,351,421 B2 | 4/2008 | Sung et al. |
| 7,572,788 B2 | 8/2009 | Glick |
| 7,638,624 B2 | 12/2009 | Glick |
| 7,683,046 B2 | 3/2010 | Glick |
| 7,851,465 B2 | 12/2010 | Glick |
| 2002/0025946 A1 | 2/2002 | Buchanan |
| 2002/0048566 A1 | 4/2002 | El-Deiry |
| 2002/0128208 A1 | 9/2002 | Snyder |
| 2003/0044776 A1 | 3/2003 | Dykens |
| 2003/0119029 A1 | 6/2003 | Glick |
| 2004/0009972 A1 | 1/2004 | Ding |
| 2004/0087489 A1 | 5/2004 | Ruiz |
| 2004/0157833 A1 | 8/2004 | Harris |
| 2004/0176358 A1 | 9/2004 | Glick |
| 2005/0113460 A1 | 5/2005 | Glick |
| 2005/0261176 A1 | 11/2005 | Glick |
| 2005/0272723 A1 | 12/2005 | Glick |
| 2006/0025388 A1 | 2/2006 | Glick |
| 2006/0052369 A1 | 3/2006 | Glick |
| 2006/0166975 A1 | 7/2006 | Glick |
| 2007/0036854 A1 | 2/2007 | Glick |
| 2007/0043033 A1 | 2/2007 | Glick |
| 2007/0105844 A1 | 5/2007 | Glick |
| 2007/0111994 A1 | 5/2007 | Glick |
| 2007/0135418 A1 | 6/2007 | Glick |
| 2007/0299059 A1 | 12/2007 | Glick |
| 2008/0064686 A1 | 3/2008 | Durrani |

FOREIGN PATENT DOCUMENTS

| | | |
|---|---|---|
| CA | 2524394 | 7/2011 |
| DE | 1810423 | 10/1969 |
| EP | 0 349 949 | 1/1990 |
| EP | 0227539 | 5/1990 |
| EP | 0 906 907 | 7/1999 |
| EP | 1143946 | 10/2001 |
| EP | 1423122 | 2/2003 |
| EP | 1398033 | 3/2004 |
| EP | 1398033 | 6/2004 |
| EP | 1622684 | 2/2006 |
| EP | 1742460 | 7/2006 |
| EP | 1778204 | 5/2007 |
| EP | 1786429 | 5/2007 |
| EP | 1845996 | 10/2007 |
| GB | 1363735 | 8/1974 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 97/01560 | 1/1997 |
| WO | 97/30992 | 8/1997 |
| WO | 98/14192 | 4/1998 |
| WO | 98/57161 | 12/1998 |
| WO | 99/19306 | 4/1999 |
| WO | 99/29347 | 6/1999 |
| WO | 99/58117 | 11/1999 |
| WO | 99/66958 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 02/098865 | 12/2002 |
| WO | 03/015703 | 2/2003 |
| WO | 03/014658 | 5/2003 |
| WO | 03/045901 | 6/2003 |
| WO | 03/050261 | 6/2003 |
| WO | 03/106628 | 12/2003 |
| WO | 2004/050610 | 6/2004 |
| WO | 2005/004988 | 1/2005 |
| WO | 2006/007532 | 1/2006 |
| WO | 2006/014526 | 2/2006 |
| WO | 2006/029245 | 3/2006 |
| WO | 99/67220 | 7/2006 |
| WO | 2006/073448 | 7/2006 |
| WO | 2006/074358 | 7/2006 |
| WO | 2006/053193 | 5/2007 |
| WO | 2007/050587 | 5/2007 |
| WO | 2007/053725 | 5/2007 |
| WO | 2007/146167 | 12/2007 |
| WO | 2008/012553 | 9/2008 |
| WO | 2008/116156 | 9/2008 |
| WO | 2008/133635 | 11/2008 |
| WO | 2009/036175 | 3/2009 |
| WO | 2009/061916 | 5/2009 |

OTHER PUBLICATIONS

Dacaudin, D. (2004) 15(8):737-745.
Bonnot, O., et al., (2003) Encephale. 29(6):553-559.
International Search Report and Written Opinion, PCT/US2008/082629, mailed Jun. 1, 2009.
Lacapere, J.J., et al. (2003) Steroids 68(7-8):569-585.
Galiegue, S., et al. (2003) Curr. Med. Chem (10(16):1563-1572.
Papadopoulo, V. (2003) Ann. Pharm. Fr. 61(1):30-50.
Goethals, I., et al. (2003) Eur. J. Nucl. Med. Mol. Imaging 30(2):325-328.
Casedo, M., et al. (2002) J. Exp. Med. 196(9):1121-1125.
Buffett-Jerrott S.E. et al. (2002) Curr. Pharm. Des. 8(1):45-58.
Smyth, W.F., et al. (1998) Electrophoresis 19(16-17):2870-2882.
Yoshii, M., et al. (1998) Nihon Shinkeo Seishin Yakurigaku Zasshi, 18(2):49-54.
Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.
Varani, J., et al. (2001), J. Invest. Dermatol., 117:1335-1341.
Varani, et al., (1994), J. Clin. Invest., 94:1747-1753.
Griffith, C.E., Br. J. Dermatol., Apr. 2001; 144(4):679-81.
Stern, R.S. (1995), dERMATOL. cLIN. 13:717-722.
Fry, L (1988), Brit. J. Dermatol., 119:445-461.
Krueger GC, et al., (1984), J. Am. Acad. Dermatol., 11:937-947.
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.
Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia," Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/US05/24060, dated Dec. 13, 2006.
International Search Report, International Patent Application No. PCT/US02/26171 dated Aug. 8, 2003.

International Search Report, International Patent Application No. PCT/US01/11599 dated Mar. 6, 2001.

International Search Report, International Patent Application No. PCT/US005/031942 dated Sep. 21, 2006.

Kerver et al, "In situ detection of spontaneous superoxide anion and singlet oxygen production by mitochondria in . . . ", Histochem. J., 29:229-237 [1997] (Abstract only).

Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-lpr/lpr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 1992.

Kozbor, et al. "The production of monoclonal antibodies from human lymphocytes", Immunol. Today, 4:72 [1983].

Lee, Sunwoo, et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)—Eds. John Wile & Sons, New York.

Malgrange, B., et al., "I•-Carbolines Induce Apoptotic Death of Cerebellar Granule Neurones in Cultures," NeuroReport 7(18):3041-3045 (1996).

Marino, M., et al., "Prevention of Systemic Lupus Erythematosus in MRL/lpr Mice by Administration of an Immunoglobulin . . . ," Nature Biotechnology—18:735-739 (2000).

MCDonnell'—349:254-256T'J et al., Progression from Lymphoid Hyperplasia to High-Grade . . . Nature—349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miernik et al., "The antimitotic activities of some benzodiazepines", Experientia, 1986, 42, pp. 956-958.

Miller, K.A., et al., "Benzodiazepines Prevent Neuronal Death by Apoptosis & Necrosis . . . ," Society for Neuroscience Abstracts—24(1-2):979 (1998).

Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," Clin. Ex p. ImmunoL 63:87-94 1986.

Okuyama, H., et al., "Effect of Cyclophosphamide Pretreatment on Defective Delayed-Type Hypersensitivity . . . ," Int Arch. Allergy Appl. Immunol. 88:394-40 (1989).

Ozols, R.F., "Paclitaxel Plus Carboplatin in the Treatment of Ovarian Cancer," Seminars in Oncology 26(1) (Supp.2:84-89 (1999).

Paola Costantini et al., "Mitochondrion as Novel Target of Anticancer Chemotherapy", JNCI Journal of the National Cancer Institute 2000 92(13): 1042-1053; doi:10. 1093/jnci/92. 13. 1042. (2000).

Parks, Daniel J. "1,4-benzodiazepine-2,5-diones as small molecule antagonists of the HDM2-p53 interaction . . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . ," Int J. Cancer—77:913-918 (1998).

Raboisson, P. "Structure-based design, synthesis and biological evaluative of novel 1,4-diazepines as HDM2 antagonists," Bioorg Med Chem. Ltrs., 15,(2005), 1857-1861.

Ramdas et al., "Benzodiazepine compounds as inhibitors of the Src protein tyrosine kinase . . . " Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune Ipr/Ipr Mice have a Defect in Antigen-Stimulated Suicide," Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA—90:4708-4712 (1993).

Schlumpf, M., et al., "Delayed Developmental Immunotoxicity of Prenatal Benzodiazepines," Toxic. In Vitro—8 (5):1061-1065(1994).

Schoemaker, H., et al., "Specific High-Affinity Binding Sites for [3H]Ro5—4864 in Rat Brain and Kidney," The J. of Pharm and Experimental Therapeutics—225(1)61-69 (1983).

Schwab, M., et al., "Amplified DNA with Limited Homology to myc Cellular Oncogene is Shared by Human Neuroblastoma Cell Lines and . . . ," Nature—305:245-248 (1983).

Scott, C.F., et al., "Comparison of Antigen-Specific T Cell Responses in Autoimmune MRL/mp-Ipr/Ipr and MRUMp-++Mice," The Journal of Immunology—1322:633-639 (1994_.

Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.

Sheppard, R.C., et al., "Acid-Labile Resin Linkage Agents for Use in Solid Phase Peptide Synthesis;" Int J. Peptide Protein Res. 20:451-454 (1982).

Snyder, Jane R., et al, "Dissection of melanogenesis with small molecules identifies prohibition as a regulator", Chemistry & Biol. 12:477-484, 4(2005).

Stevens, S.Y., et al., "Non Nucleic Acid Inhibitors of Protein-DNA Interactions Identified Through Combinatorial Chemistry," J. Am. Chem.Soc.—118:10650-10651 (1996).

Sugimoto, T., et al., Determination of Cell Surface Membrane Antigens . . . JNCI—73: (1):51-57 (1984).

Swanson et al, "Ligand recognition by anti-DNA Autoantibodies," Biochemistry, 35:1624-1633 [1996] (Abstract only).

Swanson, P.C., et al., "Ligand Recognition by Murine Anti-DNA Autoantibodies," J. Clin. Invest 97(7):1748-1760 (1996).

Swanson, P.C.,et al., "High Resolution Ephope Mapping of an Anti-DNA Autoantibody Using Model DNA Ligands," J. Immunology 71 152(5):2601-2612 (1994).

Takahashi, T., et al., "Generalized Lymphoproliferative Disease in Mice, Caused by a Point Mutation in the Fas Ligand;" Cell 76:969-976 (1994).

Tanimoto, Y., et al., Benzodiazepine Receptor Agonists Modulate Thymocyte Apoptosis Through Reduction of the Mitochondrial . . . Jpn. J. Pharmacol. 79:177-183 (1999).

Taupin, V., et al., Endogenous Anxiogenic peptide, ODN-Diazepam-Binding Inhibitor, and Benzodiazepines . . Lymphokine and Cytoklne Research 10(1):7-13 (1991).

Theoffopoulous, AN, et al., "Murine Models of Systemic Lupus Erythematosus," Advances in Immunology 37:269-390 (1985).

Bhagavathula, Narasimharao, et al., "7-Chloro-t-(4-hydroxyphenyl_-1-methyl-3-(naphthalen-2-ylmethyl) . . . ", J. Pharmacol & Exp Ther 324: 938-947 (2008).

Borea, "Stereochemical Features Controlling Binding and Intrinsic Activity Properties of Benzodiazepine Receptor Ligands", Molecular Pharmacology, Apr. 1987, 31 (4), pp. 334-344, p. 344, Abstract.

Mahrle, et al., Br. J. Bermatol. 1974, 91, 529-540.

Mui et al. Br. J. Dermatol. 1975, 92, 255-262.

EP Search Report dated Nov. 26, 2009, EP Patent Application No. 09003224.4.

Nadin, Alan, et al., "New Synthesis of 1,3-Dihydro-1,4-benzodiazepin-2(2H)-ones and 3-Amino-1,3-dihydro-1,4-benzodiazepin-2(2H)-ones: Pd-Catalyzed Cross-Coupling of Imidoyl Chlorides with Organoboronic Acids," J. Org. Chem., 2003, 68, pp. 2844-2852.

Reddy, Pavan, et al., "Interleukin-18 Regulates Acute Graft-Versus-Host Disease by Enhancing Fas-mediated Donor T Cell Apoptosis," J. Exp. Med., 2001, 194: 1433-1440.

Bossu, et al., "IL-18 cDNA vaccination protects mice from spontaneous lupus-like autoimmune disease," PNAS 2003, 100: 14181-14186.

De Bandt, et al., "Systemic lupus erythematosus induced by anti-tumour necrosis factor alpha therapy: a French national survey," Arthritis Res. & Ther., 2005, 7: R545-R551.

Abunasser, et al., "Etanercept-Induced Lupus Erythematosus Presenting as a Unilateral Pleural Effusion," Chest 2008, 134: 850-853.

Busca, et al., "Recombinant human soluble tumor necrosis factor receptor fusion protein as treatment for steroid refractory graft-versus-host disease following allogeneic hematopoietic stem cell transplatation," Am. J. Hematol., 2007, 82: 45-52.

Kyungjin, Kim, Steven K. Volkkan, and Jonathan A. Ellman, Synthesis of 3-Substituted 1,4-Benzodiazepin-2-ones, J. Braz. Chem. Soc. vol. 9(4), 375-379 (1998).

Kluge, et al., "Kinetics of Inactivation of the F1F0 ATPase of Propionigenium modestum by Dicyclohexylcarbodiimide in Relationship to H+ and Na+ Concentration: Probing the Binding Site for the Coupling Ions," Biochemistry 1993, 32, 10378-10386.

Covelli, Vito, "Stress, Neuropsychiatric Disorders and Immunological Effects Exerted by Benzodiazepines," Immunopharmacology and Immunotoxicology, 20(2), 199-209 (1998).

EP Search Report dated Jun. 23, 2010, EP Patent Application No. 10 003 823.1.

EP Search Report dated Aug. 10, 2010, EP Patent Application No. 08731682.4.

Office Action Mailed Apr. 3, 2009, U.S. Appl. No. 11/176,719, filed Jul. 6, 2005.

Office Action Mailed Aug. 19, 2009, U.S. Appl. No. 11/176,719, filed Jul. 6, 2005.

Office Action Mailed May 24, 2010, U.S. Appl. No. 11/176,719, filed Jul. 6, 2005.

Tarpley, et al., J. Chroni Diseases (1965), 18 (abstract only).

Dourlat, et al., "Novel 1,4-benzodiazepine derivaties with antiproliferative properties on tumor cell lines," Bioorganic & Medicinal Chemistry Letters, 2007, vol. 17, Issue 9, pp. 2527-2530.

Elz et al., 1989 Eur. J. Med Chem. 259-262.

Atwal et al., Tet Lett. 30, 1989, 7313.

Johnson, K.M., et al., Chemistry & Biology, 2005, 12:486-496.

Adachi, M., et al., "Aberrant Transcription Caused by the Insertion an Early Transposable Element . . . ," PNAS. USA—90:1756-1760 (1993).

Adelman, N.E., et al., Treatment of (NZB X NZW)F1 Disease with Anti-I-A Monoclonal Antibodies; J. Exp. Med.—158:1350.1355 (1983).

Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).

Atwal, K.S., et al., "Small Molecule Mitochondrial F1F0 ATPase Huydrolase Inhibitors as Cardioprotective Agents" J. Med. Chem. 47, pp. 1081-1084 (2004).

Baader, S.L., et al., Uptake and Cytotoxicity of Ascorbic Acid and Dehydroascorbic Acid . . . Anticancer Research—14:221-228 (1994).

Beale, P.J., et al., "BCL-2 Family Protein Expression and Platinum Drug Resistance in Ovarian Carcinoma," British Journal of Cancer—82 (2) :436-440 (2000).

Beurdeley-Thomas, et al., "The peripheral benzodiazepine receptors: a review," Journal of Neuro-Oncology 46 (2000) 45-56.

Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.

Blum, P., et al., "Stiff-Person Syndrome: An Autoimmune Disease," Movement Disorders 6(1):12-20 (1991).

Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.

Bono et al., "Peripheral benzodiazepine receptor agonists exhibit potent antiapoptotic activities," Biochemical and Biophysical Research Communications, 1999, 265, pp. 457-461.

Boojamra, C.G., et al., "Solid-Phase Synthesis of 1,4. Benzodiazepine-2,5-Diones. Library Prep. and Demonstration of Synthesis Generality," J. Org. Chem.—62:1240-1256 (1997).

Bunin et al., "Synthesis and evaluation of 1,4-benzodiazepine libraries", Methods in Enzymology, 1996, 267, pp. 448-465.

Bunin, B.A., et al., "The Combinatorial Synthesis and Chemical and Biological Evaluation of a 1,4-Benzodiazepine Libra," PNAS USA—91:4708-4712 (1994).

Bunin, BA., et al., "A General and Expedient Method for the Solid-Phase Synthesis of 1,4-Benzodlazepine Derivatives," J. Am. Chem. Soc.—114:10997-10998 (1992).

Chumakov,A.M., et al., "Analysis of p53 Transactivation Through High-Affinity Bindir•g Sites," Oncogene—8:3005o3011 (1993).

Churcher et al., "A new series of potent benzodiazepine y-Secretase inhibitors," Bioorganic & Medicinal Chemistry Letters 13 (2003) 179-.

Cohen, P.L., et al., "Lpr and gld: Single Gen• Models of Systemic Autoimmunity and Lymphoproliferative Disease," Annu. Rev. Immunol. 9:243-269 (1991).

Cole et al., "The EBV-Hybridoma Technique and its Application to Human Lung Cancer", Monoclonal Antibodies and Cancer Therapy, Alan R. Liss, Inc., pp. 77-96 [1985].

Colosi, et al,"Mutational analysis of the intracellular domain of the human growth hormone recetor", J. Biol. Chem., 268:12617 [1993].

Crabtree, R.H., "A New Type of Hydrogen Bond," Science 282:2000-2001 1998.

Darrow et al., "Structurally similar small molecule photoaffinity CCK-A Agonists and Antagonists as Novel Tools . . . ", Bioorganic & Medicinal Chemistry Letters 8 (1998) 3127-3132.

Desoize, B., "Anticancer Drug Resistance and Inhibition of Apoptosis," Anicancer Research—14:2291-2294 1994.

Dichek, David A., et al., "Seeding of intravascular stents with genetically engineered endothelial cells," Laboratory Investigation, 80:5 pp. 1347-1353 (1989).

Doble, A., et al., "Labelling of Peripheral-Type Benzodiazepine B Human Brain with [aH]I 1195: Anatomical and Subcellular Distribution," Brain Research Bulletin,18:49-61 1987.

Don, A. et al., Cancer Cell, vol. 3, May(2003) 497-509.

Donadio, J.V., et al., "Immunosuppressive Drug Therapy in Lupus Nephritis," American Journal of Kidney Diseases 21 (3):239-250 1993.

Ermak, T.H., et al., "Treatment of Murine Lupus with Monoclonal Antibody to L3T4," Laboratory Investigation 61(4):447-456 1989.

Fuh et al, "Rational design of potent antagonists to the human growth hormone receptor", Science, 256:1677 [1992].

Gallant, J.E., et al.,"Incidence and Natural History of Cytomegalovirus Disease in Patients with Advanced Human . . . " The Journal of Infect. Disease, 166: 1223-122 (1992).

Garcia-Calvo, M., et al. "Inhibition of Human Caspases by Peptide-Based and Macromolecular Inhibitors," The Journal of Biological Chemistry 273(49):32608-32613 1998.

Gorczyca, W., et al., "Induction of DNA Slrand Breaks Associated with Apoptosis During Treatment of Leukemias," Leukemia 7(5):659-670 1993.

Gordon, C., et al.. "Chronic Therapy with Recombinant Tumor Necrosis Factor-or in Autoimmune NZB/NZW Fi Mice," Clinical Immunology and Immunopatholoy—52:421-434 (1989).

Gordon, E.M., et al., Applications of Combinatorial Technologies to Drug Discovery. 2. Combinatorial Organic 52 Synthesis, Library Screening . . . Journal of Med. Chem. 37(10): (1994).

Grasberger, Bruce L., "Discovery and cocrystal structure of benzodiazepinedione HDM2 antagonists that activate p53 in cells", J. Med. Chem., 48, (2005), 909-912.
Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.
Hahn, B.H., et al.; "Influence of Cyclophosphamide and Other Immunosuppressive Drugs on Immune Disorders . . . ," Arthritis and Rheumatism—18(2):145-152 (1975).
Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).
Hang, L., et al., "A Spontaneous Rheumatoid Arthritis-Like Disease in MR/1 Mice," J. Exp. Mod. -155:1690-1701 1982.
Herranz, R., "Cholesystokinin Antagonists: Pharmacological and Therapeutic Potential", Medicinal Research Reviews 23 (2003) 559-603.
Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).
Horowitz, R.E., et al., "Cyclophosphamide Treatment of Mouse Systemic Lupus Erythematosus," Laboratory Investigation 21 (3): 199-206 1969.
Hulme, C. J. "Improved procedure for the solution phase preparation of 1,4-benzodiazepine-2,5-dione libraries . . . ", Org. Chem., 63,(1998), 8021-8023.
Huse et al., "Generation of a Large Combinatorial Library of the Immunoglobulin Repertoire in Phage Lambda", Science, 246:1275-1281 [1989].
International Search Report and Written Opinion of PCT/US2008/057827 dated Oct. 6, 2008.
IPER and ISR for PCT/us02/31942 mailed Feb. 2, 2007.
Itoh, N., et al., "The Polypeptide Encoded by the cDNA for Human Cell Surface Antigen Fas Can Mediate Apoptosis," Cell 66:233-243 (1991).
Jones, The non-conalent interaction of pyrrolo[2,1-c][benzodiazepines-5, 11-diones with DNA, Anti-Cancer Drug Design, 5:249-264 (1990).
Kamal, A., "Synthesis of DNA-interactive Pyrrolo[2,1-c][1,4] benzodiazepines by employing polymer-supported reagents . . . ," Synlett, 14,(2004), 2533-35.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Written Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiner's Report, AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.

Nawrocka, et al., Arch. Pharm. (Weinheim) Jan. 2001, 334(1), 3-10.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
Godic, "New approaches to psoriasis treatment. A review." 2004. Acta Dermatoven APA, vol. 13, No. 2, pp. 50-57.
Bisaha, S.N., et al., A switch in enantiomer preference between mitochondrial F1F0-ATPase chemotypes, Bioorganic & Medicinal Chemistry Letters, 2005 15(11), pp. 2749-2751.
International Search Report and Written Opinion dated Mar. 27, 2009, PCT/US2008/076021.
Chinese Office Action, CN Patent Application No. 200580029827.4, dated Apr. 17, 2009.
AU Patent Application No. 2006203946 Examiner's Report dated Sep. 10, 2008.
EP Search, EP Patent Application No. 05856659, mailed Dec. 9, 2008.
Iiangumaran, et al., "CD44 Selectively Associates with Active Src Family Protein Tyrosine Kinases Lck and Lyn in Glycosphingolipid-Rich . . . ", Blood, vol. 91, No. 10 (May 15, 1998), pp. 3901-3908.
Sato, et al., "CD22 negatively and positively regulates signal transduction through the B lymphocyte antigen receptor," seminars in Immunology, vol. 10, 1998, pp. 287-297.
Joshi, et al., "Oligomycin Sensitivey-conferring Protein (OSCP) of Mitochodrial ATP Synthase," The Journal of Biological Chemistry, vol. 267, No. 18,m Issue of Jun. 25, pp. 12860-12867, 1992.
Giuseppe Piedimonte, et al., "Association of Tyrosine Protein Kinase Activity With Mitochondria in Human Fibroblasts," Journal of Cellular Biochemistry 32:113-123 (1986).
EP Search, EP Patent Application No. 04 775 923.8, dated Dec. 15, 2008.
Appleby, et al., "Murine chronic graft-versus-host disease as a model of osystemic lupus erythematosus: effect of immunosuppressive drugs on disease development," Clin. Exp. Immunol. (1989) 78, 449-453.
Bastian, et al., "Casein Interference in Bovine Plasmin Assays Using a Synthetic Substrate," (1991) J Dairy Sci 74:4119-4124.
Johnson, et al., "Mechanistic Basis for Therapeutic Targeting of the Mitochondrial FF-ATPase", downloaded from http://pubs.acs.org on Dec. 5, 2008, ASC Chem. Biol. 1 (5), 304-308, Publication Date (Web): Jun. 9, 2006.
EP Supplementary Search Report, EP Application No. 02794914.8 dated Nov. 6, 2008.
Lee, et al., J. Org. Chem. 1999, 64, 3060-3065.
Solomko, et al., Chemistry of Heterocyclic Compounds, vol. 11, No. 11, Nov. 1975, pp. 1231-1248.
EP Patent Application No. 05 80 4417 Supplementary European Search Report dated Mar. 26, 2009.
Algarra, et al., "Application of the Photo-Fries Rearrangement of Aryl N-Chloroacetylanthranylates as Key Step in the . . . ", Heterocycles, vol. 36 1993, pp. 2335-2344.
EP Patent Application No. 06 717616 Supplementary Search Report dated Mar. 26, 2009.
Levitzki, Alexander, "Protein Tyrosine Kinase Inhibitors as Novel Therapeutic Agents," Pharmacol. Ther. vol. 82, Nos. 2-3, pp. 231-239 (1999).
Sanchez, et al., "Tumorigenic activity of the BCR-ABL oncogenes is mediated by BCL2" Proc Natl Acad Sci U S A (Jun. 6, 1995) 92(12) 5287-5291.
Ji Yang, et al., "Prevention of Apoptosis by BCL-2; Release of Cytochrome c from Mitochondria Blocked" Science vol. 275, No. 5303, pp. 1129-113221 (1997).

Prindull, "Apoptosis in the embryo and tumorigenesis" European Jouranl of Cancer, vol. 31, Issue 1 (1995) pp. 116-123.

Francis, T.M., et al., "Identification of cytotoxic, T-cell-selective 1,4-benzodiazepine-2,5-diones," Bioorganic & Medicinal Chemistry Letters, Pergamon, Elsevier Science, GB, vol. 16, No. 9, May 1, 2006, pp. 2423-2427.

Akssira, M., et al., "New Routes to 1,4-benzodiazepin-2,5-diones," Tetrahedron (1994), vol. 50, No. 30, pp. 9051-9060.

Mohiuddin, G., et al., "A Versatile Synthesis of 3H-1(H), 4(H)-Benzodiazepin-2,5-diones," Indian Journal of Chenmistry, 1985, vol. 24B, pp. 905-907.

Boojamra, Constantine G., et al., "An Expedient and High-Yielding Method for the Solid-Phase Synthesis of Diverse 1,4-Benzodiazepine-2, 5-diones," Journal of Organic Chemistry, 1995, vol. 60, No. 18, pp. 5742-5743.

Keating, Thomas A., et al., "A Remarkable Two-Step Synthesis of Diverse 1, 4-Benzodiazepine-2, 5-diones Using the Ugi Four-Component Condensation," Journal of Organic Chemistry, 1996, vol. 61, No. 25, pp. 8935-8939.

Juaristi, Eusebio, et al., "Enantioselective Synthesis of α-Amino Acides from Chiral 1, 4-enzodiazepine-2, 5-diones Contianing the α-Phenethyl Group," Journal of Organic Chemistry, 1999, Mar. 26, vol. 64, No. 8, pp. 2914-2918.

Marc, Gasper, et al., "High Yield Phase Transfer N-Alkylation of Some Benzodiazepinese by Esters of ω-Halo Acids," Synthetic Communications, 1998, vol. 28, No. 7, pp. 1143-1157.

Bolli, M.N., et al., "Novel Benzo[1,4]diazepin-2-one-Derivatives as Endothelin Receptor Antagonists", Journal of Medicinal Chemistry, vol. 47, No. 11, Apr. 23, 2004, pp. 2776-2795.

Cunha, 2006, "The first bismuth(III)-catalyzed guanylation of thioureas", Tetrahedron Letters 47:6955-56.

Cunha, 2002, "Bismuth nitrate pentahydrate: a new and environmentally benign reagent for guanidylation of N-benzoylthioureas", Tetrahedron Letters 43: 49-52.

Yano, Masafumi, et al., "Effect of Milrinone on Left Ventricular Relaxation and Ca2+ Update Function of Cardiac Sarcoplasmic Reticulum," Am. J. Physiol. Heart Circ. Physiol, 279: H1898-H1905 (2000).

Gatza, et al., "Manipulating the Bioenergetics of Alloreactive T Cells Causes Their Selective Apoptosis and Arrests Graft-Versus-Host Disease," Sci. Transl. Med. 3(67ra8): 1-8 (2011).

Shoemaker, et al., "The NC160 Human Tumour Cell Line Anticancer Drug Screen," Nat. Rev. Cancer 6:813-823 (2006).

Brittain, H.G., Polymorphism in Pharmaceutical Solids (1999), published by Marcel Dekker, Inc. (New York, USA), Chapter 5, pp. 205-208.

Byrn, S.R., et al. Solid-State Chemistry of drugs. 2nd ed. (1999), published by SSCI, Inc. (Indiana, USA).

Shoemaker, Hans, et al., "Specific High-Affinity Binding Sites for [3H]Ro 5-4864 in Rat Brain and Kidney," The Journal of Pharmacology and Experimental Therapeutics, vol. 225, No. 1 (1983).

Boitano, Anthony, et al., "The Proapoptotic Benzodiazepine Bz-423 Affects the Growth and Survival of Malignant B Cells," Cancer Research 63, 6870-6876 (Oct. 15, 2003).

Munoz, et al., "Autoimmunity and chronic inflammation—two cleaance-related steps in the etiopathogenesis of SLE", Autoimmunity Reviews 10 (2010) pp. 38-42.

BENZODIAZEPINONE COMPOUNDS USEFUL IN THE TREATMENT OF SKIN CONDITIONS

CROSS-REFERENCE TO RELATED APPLICATIONS

This application is a continuation of pending U.S. patent application Ser. No. 12/266,239, filed Nov. 6, 2008, which claims the benefit of priority to expired U.S. Provisional Patent Application No. 60/985,898, filed Nov. 6, 2007, the contents of which are hereby incorporated by reference in their entireties.

STATEMENT REGARDING FEDERALLY SPONSORED RESEARCH OR DEVELOPMENT

This invention was made with government support under Grant Number AI47450 awarded by the U.S. Department of Health & Human Services. The government has certain rights in the invention.

FIELD OF THE INVENTION

The present invention relates generally to the field of pharmaceutical compounds useful in treating aberrant skin conditions. More specifically, the present invention relates to benzodiazepinone compounds and methods of using the same to treat skin conditions associated with epidermal hyperplasia, such as psoriasis.

BACKGROUND OF THE INVENTION

Aberrant skin conditions afflict millions of people worldwide. Patients suffering from a skin condition often experience pain and/or discomfort due to the condition. For some patients, the pain or discomfort can be quite severe. A patient's ability to sleep, perform routine tasks, and/or participate in certain sports can be affected by some skin conditions. In addition to physical ailments, skin conditions can have a detrimental affect on a patient's psychological well-being. For instance, some skin conditions cause unsightly sores on a patient's skin, causing some patients to avoid social interaction and/or become emotionally depressed. Rosacea is one such condition that can have psychological effects because it often causes red discoloration of the face and the appearance of unsightly, acne-like pimples.

One characteristic of numerous skin conditions is epidermal hyperplasia. Epidermal hyperplasia is an abnormal increase in the number of normal cells in normal arrangement in epidermal tissue. Research has demonstrated that excessive growth of keratinocyte cells is commonly associated with epidermal hyperplasia. It is postulated that epidermal hyperplasia involves a complex multi-cellular inflammatory event. However, topical treatment of all-trans retinoic acid (RA) or its precursor, all-trans retinol (ROL), to the skin also results in epidermal hyperplasia. See, e.g., Varani J, et al., (2001) *J. Invest. Dermatol*, 117:1335-1341. Representative skin conditions associated with epidermal hyperplasia include psoriasis and atopic dermatitis. See, e.g., Krueger G C, et al., (1984) *J. Am. Acad. Dermatol*. 11: 937-947; Fry L. (1988), *Brit. J. Dermatol*. 119:445-461

Psoriasis is a chronic, inflammatory, hyperproliferative skin condition that affects approximately 2% of the general population. Approximately 150,000 new cases of psoriasis and approximately 400 deaths from psoriasis are reported each year. See Stern, R. S. (1995) *Dermatol. Clin*. 13:717-722. Typical symptoms of psoriasis include skin lesions, redness, inflammation, or patches of skin that become dry, red, covered with silvery scales, cracked, and/or painful. Additional symptoms include joint pain or aching, although these symptoms are typically associated with psoriatic arthritis. Psoriasis can affect all parts of the skin, but it is more commonly seen on the skin of the trunk, scalp, elbows, knees, or in the fingernails or toenails. The symptoms of psoriasis may become worse in response to cuts, burns, insect bites or other skin injuries. The symptoms of psoriasis can also be more severe in patients having a deficient immune system, such as patients afflicted with AIDS or receiving cancer chemotherapy.

There are a several of types of psoriasis. The most common type of psoriasis is chronic plaque syndrome. This type of psoriasis consists of periods of remission and relapse during the course of the condition. If left untreated, plaque psoriasis can evolve into a more severe condition, such as pustular psoriasis or erythrodermic psoriasis. In pustular psoriasis, the red areas on the skin contain blisters with pus. Erythrodermic psoriasis is characterized by large patches of skin that are red and scaling. Patients suffering from erythrodermic psoriasis often complain that the affected patches of skin are itchy and/or painful. Inverse psoriasis is characterized by smooth, inflamed areas of skin, typically appearing in skin folds. Guttate psoriasis appears as numerous, teardrop-shaped spots on the skin and is often associated with streptococcal throat infection. Nail psoriasis is characterized by changes in the finger and toe nails. This form of psoriasis often involves discoloring under the nail or thickening of the skin under the nail.

The current methods for treating psoriasis suffer from a number of drawbacks. For example, many of the currently-available, topical anti-psoriatic agents irritate the skin, cannot be used for extended durations, and/or lead to aggressive recurrence of the psoriatic condition if treatment is terminated abruptly. Anti-inflammatory agents, although capable of alleviating certain symptoms, do not cure the underlying disease. Another current treatment option, photochemotherapy, can lead to squamous-cell and melanoma skin cancer.

Accordingly, the need exists for new compositions and methods that are effective in treating skin conditions, such as psoriasis.

SUMMARY OF THE INVENTION

The present invention provides benzodiazepinone compounds, methods for treating various conditions using benzodiazepinone compounds, and methods for reducing the proliferation of a keratinocyte cell using benzodiazepinone compounds.

In one aspect, the invention provides a compound represented by Formula I:

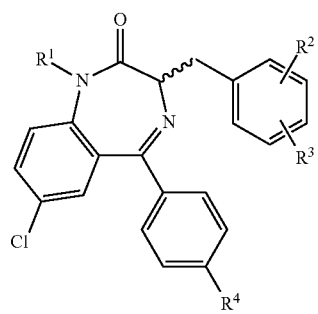

including salts, esters and prodrugs thereof, wherein
R¹ is H or $C_{1-6}$ alkyl;
R² is H or $C_{1-6}$ alkyl;
R³ is $C_{1-6}$ alkyl;
R⁴ is hydroxyl or fluoro;
the stereochemical configuration at a stereocenter in a compound represented by formula I is R, S, or a mixture thereof; and
provided that said compound is not

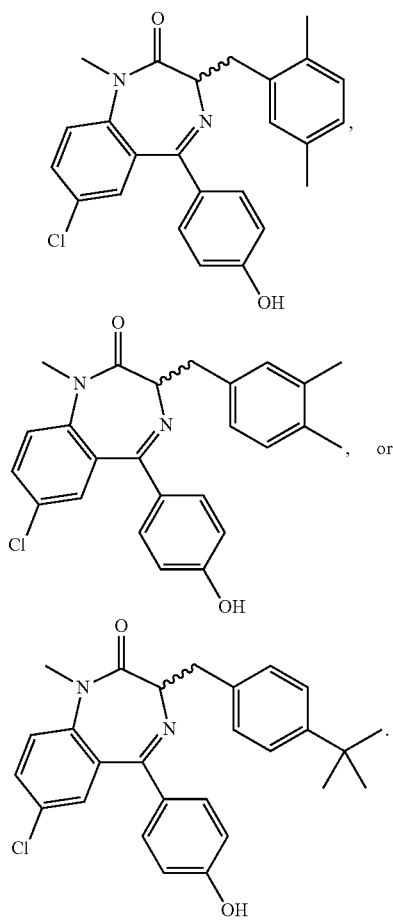

The family of compounds embraced by formula I can be present in pharmaceutical compositions comprising a compound described herein and a pharmaceutically acceptable carrier. In certain embodiments, the pharmaceutical composition further comprises a steroid, cyclosporine, vitamin D, vitamin D analog, keratolytic agent, topical retinoid, calcineurin inhibitor, or coal tar.

In another aspect, the invention provides a method of treating a skin condition. The method comprises administering a therapeutically effective amount of a compound of formula I, described herein, to a subject in need thereof to ameliorate a symptom of the condition. A variety of skin conditions can be treated, particularly those associated with epidermal hyperplasia. In certain embodiments, the skin condition is atopic dermatitis, rosacea, or psoriasis.

In another aspect, the invention provides a method of treating epidermal hyperplasia. The method comprises administering a therapeutically effective amount of compound of formula I, described herein, to a subject in need thereof to ameliorate a symptom of the epidermal hyperplasia.

In certain embodiments, the invention provides a combination therapy. For instance, in certain embodiments, one of the aforementioned methods further comprises administering to the subject a therapeutic agent selected from the group consisting of a steroid, cyclosporine, vitamin D, vitamin D analog, keratolytic agent, topical retinoid, calcineurin inhibitor, and coal tar. A variety of different steroids, cyclosporines, vitamin D analogs, keratolytic agents, topical retinoids, calcineurin inhibitors and coal tars are amenable to the present invention. In certain embodiments, the steroid is a topical corticosteroid. In certain embodiments, the topical corticosteroid is triamcinolone acetonide or betamethasone dipropionate; the vitamin D analog is calcipotriene; the keratolytic agent is anthralin; the topical retinoid is tretinoin or tazarotene; and the calcineurin inhibitor is tacrolimus, pimecrolimus, ascomycin, or ISA247.

In another aspect, the invention provides a method of reducing the proliferation of a keratinocyte cell. The method comprises exposing a keratinocyte cell to a compound of formula I, described herein.

DETAILED DESCRIPTION OF THE INVENTION

Definitions: To facilitate an understanding of the invention, the following terms have the meanings defined below.

The term "benzodiazepine" refers to a seven-membered non-aromatic heterocyclic ring fused to a phenyl ring wherein the seven-membered ring has two nitrogen atoms, as part of the heterocyclic ring. The two nitrogen atoms are in 1 and 4 positions, as shown in the general structure below.

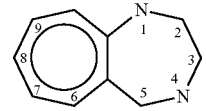

The benzodiazepine can be substituted with one keto group (typically at the 2-position), or with two keto groups, one each at the 2- and 5-positions. For purposes of the present invention, the benzodiazepine compounds encompass various substituents at the seven-membered non-aromatic heterocyclic ring.

The term "alkyl" is art-recognized, and includes saturated aliphatic groups, including straight-chain alkyl groups, branched-chain alkyl groups, cycloalkyl groups, alkyl substituted cycloalkyl groups, and cycloalkyl substituted alkyl groups. Representative examples include methyl, ethyl, propyl, isopropyl, butyl, isobutyl, s-butyl, t-butyl, pentyl, hexyl, cyclopropyl, cyclobutyl, cyclopentyl, cyclohexyl, and cyclopropylmethyl.

The term "hydroxyl" means —OH. For example, pentane substituted with a hydroxyl group has the formula $CH_3(CH_2)_3CH_2OH$.

The term "pharmaceutical composition" refers to the combination of an active agent with a carrier, inert or active, making the composition especially suitable for diagnostic or therapeutic use in vivo or ex vivo.

The term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

The term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while sometime not in themselves pharmaceutically acceptable, may be employed in the preparation of salts useful as intermediates in obtaining the compounds of the invention and their pharmaceutically acceptable acid addition salts. Examples of bases include alkali metals (e.g., sodium) hydroxides, alkaline earth metals (e.g., magnesium), hydroxides, ammonia, and compounds of formula $NW_4^+$, wherein W is $C_{1-4}$ alkyl, and the like. Examples of salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

It will be noted that the structure of some of the compounds of the invention includes asymmetric carbon atoms. It is to be understood that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The terms ortho, meta and tiara are art-recognized and refer to 1,2-, 1,3- and 1,4-disubstituted benzenes, respectively. For example, the names 1,2-dimethylbenzene and ortho-dimethylbenzene are synonymous.

As a general matter, compositions specifying a percentage are by weight unless otherwise specified. Further, if a variable is not accompanied by a definition, then the previous definition of the variable controls.

The term "hyperplasia" refers to a form of cell proliferation involving an increase in cell number in a tissue or organ, without significant alteration in structure or function. Pathologically, hyperplasia involves the proliferation of cells that is not governed by the usual limitations of normal cell growth. Hyperplasia may be exhibited in hyperplastic cells or cancer cells, which includes tumor cells, neoplastic cells, malignant cells, and metastatic cells.

The term "epidermal hyperplasia" refers to an abnormal multiplication or increase in the number of normal cells in normal arrangement in epidermal tissue. Epidermal hyperplasia is a characteristic of numerous skin conditions, including but not limited to, psoriasis.

The term "keratinocyte" refers to a skin cell of the keratinized layer of the epidermis.

The term "fibroblast" refers to mesodermally-derived resident cells of connective tissue that secrete fibrillar procollagen, fibronectin and collegenase.

The term "$EC_{50}$" is art-recognized and refers to the concentration of a compound at which 50% of its maximal effect is observed.

The term "subject" refers to organisms to be treated by the methods of the present invention. Such organisms preferably include mammals (e.g., murines, simians, equines, bovines, porcines, canines, felines, and the like), and most preferably includes humans.

The term "effective amount" refers to the amount of a compound (e.g., benzodiazepinone compound) sufficient to effect beneficial or desired results. An effective amount can be administered in one or more administrations, applications or dosages and is not limited or intended to be limited to a particular formulation or administration route.

The term "second agent" refers to a therapeutic agent other than the benzodiazepinone compounds in accordance with the present invention. In certain instances, the second agent is an anti-proliferative agent.

The term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "combination therapy" includes the administration of a benzodiazepinone compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention provides benzodiazepinone compounds and methods of using such compounds as therapeutic agents to treat a number of different conditions. Exemplary compositions and methods of the present invention are described in more detail in the following sections: I. Benzodiazepinone Compounds; II. Therapeutic Applications of Benzodiazepinone Compounds; and III. Pharmaceutical Compositions, Formulations, and Exemplary Administration Routes and Dosing Considerations.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as "Comprehensive Organic Synthesis" (B. M. Trost & I. Fleming, eds., 1991-1992); "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Benzodiazepinone Compounds

In one aspect, the invention provides a compound represented by Formula I:

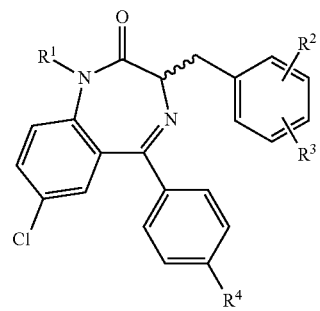

including salts, esters and prodrugs thereof, wherein $R^1$ is H or $C_{1-6}$ alkyl;

$R^2$ is H or $C_{1-6}$ alkyl;

$R^3$ is $C_{1-6}$ alkyl;

$R^4$ is hydroxyl or fluoro;

the stereochemical configuration at a stereocenter in a compound represented by formula I is R, S, or a mixture thereof; and provided that said compound is not

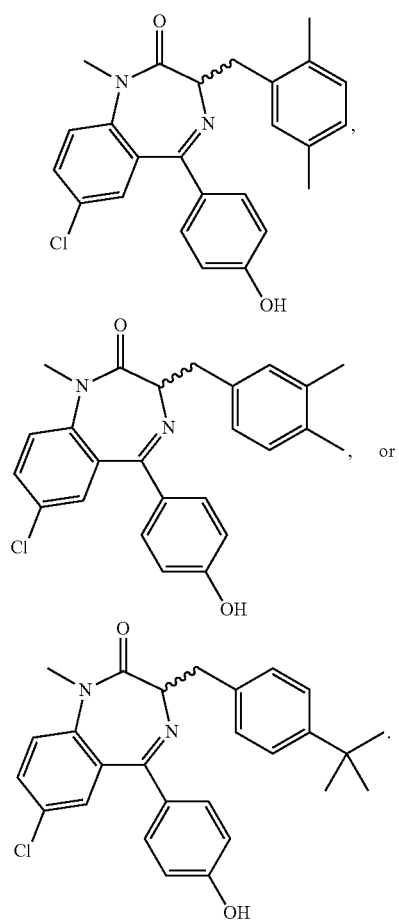

In certain embodiments, R₄ is fluoro. In certain other embodiments, the compound has the structure:

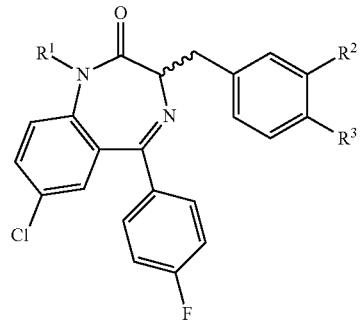

In certain other embodiments, R₄ is hydroxyl. In certain other embodiments, the compound has the structure:

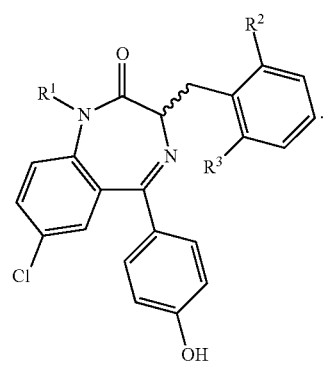

In certain other embodiments, the compound has the structure:

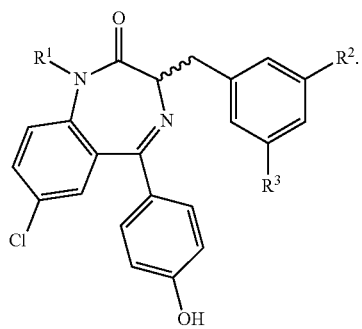

In certain other embodiments, R² and R³ are C$_{1-3}$ alkyl. In certain other embodiments, R² and R³ are methyl. In certain other embodiments, R² and R³ are ethyl. In certain other embodiments, R² and R³ are isopropyl. In certain other embodiments, R¹ is methyl. In certain other embodiments, R² is H, and R³ is isopropyl. In certain other embodiments, R¹ is H or methyl; and R² and R³ are C$_{1-3}$ alkyl. In certain other embodiments, the compound is:

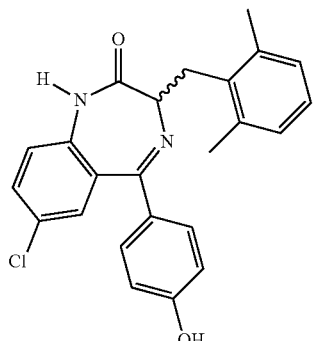

In certain other embodiments, the compound is:

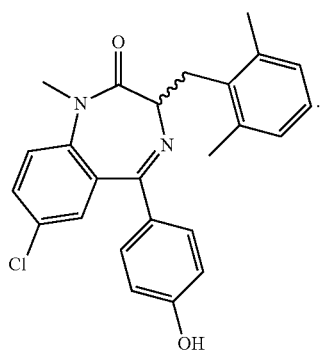 [SMILES: Cc1cccc(C)c1CC1N=C(c2ccc(O)cc2)c2cc(Cl)ccc2N(C)C1=O]

In certain embodiments, the compounds are as described in the following tables.

TABLE 1

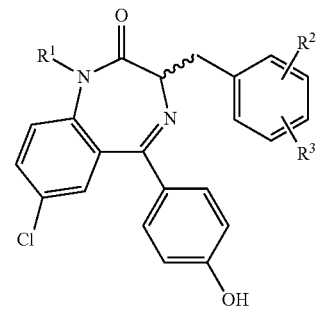

| No. | R¹ | R² | R³ |
|---|---|---|---|
| 1 | H | 2-CH₃ | H |
| 2 | H | 3-CH₃ | H |
| 3 | H | 4-CH₃ | H |
| 4 | H | 2-CH₃ | 3-CH₃ |
| 5 | H | 2-CH₃ | 4-CH₃ |
| 6 | H | 2-CH₃ | 5-CH₃ |
| 7 | H | 2-CH₃ | 6-CH₃ |
| 8 | H | 3-CH₃ | 4-CH₃ |
| 9 | H | 3-CH₃ | 5-CH₃ |
| 10 | H | 2-CH₂CH₃ | H |
| 11 | H | 3-CH₂CH₃ | H |
| 12 | H | 4-CH₂CH₃ | H |
| 13 | H | 2-CH₂CH₃ | 3-CH₂CH₃ |
| 14 | H | 2-CH₂CH₃ | 4-CH₂CH₃ |
| 15 | H | 2-CH₂CH₃ | 5-CH₂CH₃ |
| 16 | H | 2-CH₂CH₃ | 6-CH₂CH₃ |
| 17 | H | 3-CH₂CH₃ | 4-CH₂CH₃ |
| 18 | H | 3-CH₂CH₃ | 5-CH₂CH₃ |

TABLE 1-continued

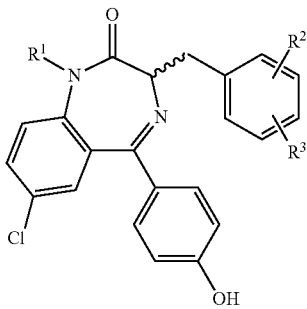

| No. | R¹ | R² | R³ |
|---|---|---|---|
| 19 | H | 2-CH(CH₃)₂ | H |
| 20 | H | 3-CH(CH₃)₂ | H |
| 21 | H | 4-CH(CH₃)₂ | H |
| 22 | H | 2-CH(CH₃)₂ | 3-CH(CH₃)₂ |
| 23 | H | 2-CH(CH₃)₂ | 4-CH(CH₃)₂ |
| 24 | H | 2-CH(CH₃)₂ | 5-CH(CH₃)₂ |
| 25 | H | 2-CH(CH₃)₂ | 6-CH(CH₃)₂ |
| 26 | H | 3-CH(CH₃)₂ | 4-CH(CH₃)₂ |
| 27 | H | 3-CH(CH₃)₂ | 5-CH(CH₃)₂ |
| 28 | CH₃ | 2-CH₃ | H |
| 29 | CH₃ | 3-CH₃ | H |
| 30 | CH₃ | 4-CH₃ | H |
| 31 | CH₃ | 2-CH₃ | 3-CH₃ |
| 32 | CH₃ | 2-CH₃ | 4-CH₃ |
| 33 | CH₃ | 2-CH₃ | 6-CH₃ |
| 34 | CH₃ | 3-CH₃ | 5-CH₃ |
| 35 | CH₃ | 2-CH₂CH₃ | H |
| 36 | CH₃ | 3-CH₂CH₃ | H |
| 37 | CH₃ | 4-CH₂CH₃ | H |
| 38 | CH₃ | 2-CH₂CH₃ | 3-CH₂CH₃ |
| 39 | CH₃ | 2-CH₂CH₃ | 4-CH₂CH₃ |
| 40 | CH₃ | 2-CH₂CH₃ | 5-CH₂CH₃ |
| 41 | CH₃ | 2-CH₂CH₃ | 6-CH₂CH₃ |
| 42 | CH₃ | 3-CH₂CH₃ | 4-CH₂CH₃ |
| 43 | CH₃ | 3-CH₂CH₃ | 5-CH₂CH₃ |
| 44 | CH₃ | 2-CH(CH₃)₂ | H |
| 45 | CH₃ | 3-CH(CH₃)₂ | H |
| 46 | CH₃ | 4-CH(CH₃)₂ | H |
| 47 | CH₃ | 2-CH(CH₃)₂ | 3-CH(CH₃)₂ |
| 48 | CH₃ | 2-CH(CH₃)₂ | 4-CH(CH₃)₂ |
| 49 | CH₃ | 2-CH(CH₃)₂ | 5-CH(CH₃)₂ |
| 50 | CH₃ | 2-CH(CH₃)₂ | 6-CH(CH₃)₂ |
| 51 | CH₃ | 3-CH(CH₃)₂ | 4-CH(CH₃)₂ |
| 52 | CH₃ | 3-CH(CH₃)₂ | 5-CH(CH₃)₂ |

TABLE 2

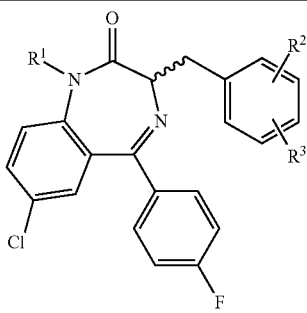

| No. | R¹ | R² | R³ |
|---|---|---|---|
| 1 | H | 2-CH₃ | H |
| 2 | H | 3-CH₃ | H |
| 3 | H | 4-CH₃ | H |
| 4 | H | 2-CH₃ | 3-CH₃ |
| 5 | H | 2-CH₃ | 4-CH₃ |
| 6 | H | 2-CH₃ | 5-CH₃ |

TABLE 2-continued

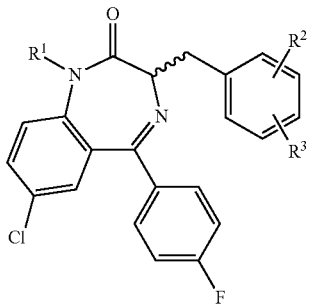

| No. | R¹ | R² | R³ |
|---|---|---|---|
| 7 | H | 2-CH₃ | 6-CH₃ |
| 8 | H | 3-CH₃ | 4-CH₃ |
| 9 | H | 3-CH₃ | 5-CH₃ |
| 10 | H | 2-CH₂CH₃ | H |
| 11 | H | 3-CH₂CH₃ | H |
| 12 | H | 4-CH₂CH₃ | H |
| 13 | H | 2-CH₂CH₃ | 3-CH₂CH₃ |
| 14 | H | 2-CH₂CH₃ | 4-CH₂CH₃ |
| 15 | H | 2-CH₂CH₃ | 5-CH₂CH₃ |
| 16 | H | 2-CH₂CH₃ | 6-CH₂CH₃ |
| 17 | H | 3-CH₂CH₃ | 4-CH₂CH₃ |
| 18 | H | 3-CH₂CH₃ | 5-CH₂CH₃ |
| 19 | H | 2-CH(CH₃)₂ | H |
| 20 | H | 3-CH(CH₃)₂ | H |
| 21 | H | 4-CH(CH₃)₂ | H |
| 22 | H | 2-CH(CH₃)₂ | 3-CH(CH₃)₂ |
| 23 | H | 2-CH(CH₃)₂ | 4-CH(CH₃)₂ |
| 24 | H | 2-CH(CH₃)₂ | 5-CH(CH₃)₂ |
| 25 | H | 2-CH(CH₃)₂ | 6-CH(CH₃)₂ |
| 26 | H | 3-CH(CH₃)₂ | 4-CH(CH₃)₂ |
| 27 | H | 3-CH(CH₃)₂ | 5-CH(CH₃)₂ |
| 28 | CH₃ | 2-CH₃ | H |
| 29 | CH₃ | 3-CH₃ | H |
| 30 | CH₃ | 4-CH₃ | H |
| 31 | CH₃ | 2-CH₃ | 3-CH₃ |
| 32 | CH₃ | 2-CH₃ | 4-CH₃ |
| 33 | CH₃ | 2-CH₃ | 5-CH₃ |
| 34 | CH₃ | 2-CH₃ | 6-CH₃ |
| 35 | CH₃ | 3-CH₃ | 4-CH₃ |
| 36 | CH₃ | 3-CH₃ | 5-CH₃ |
| 37 | CH₃ | 2-CH₂CH₃ | H |
| 38 | CH₃ | 3-CH₂CH₃ | H |
| 39 | CH₃ | 4-CH₂CH₃ | H |
| 40 | CH₃ | 2-CH₂CH₃ | 3-CH₂CH₃ |
| 41 | CH₃ | 2-CH₂CH₃ | 4-CH₂CH₃ |
| 42 | CH₃ | 2-CH₂CH₃ | 5-CH₂CH₃ |
| 43 | CH₃ | 2-CH₂CH₃ | 6-CH₂CH₃ |
| 44 | CH₃ | 3-CH₂CH₃ | 4-CH₂CH₃ |
| 45 | CH₃ | 3-CH₂CH₃ | 5-CH₂CH₃ |
| 46 | CH₃ | 2-CH(CH₃)₂ | H |
| 47 | CH₃ | 3-CH(CH₃)₂ | H |
| 48 | CH₃ | 4-CH(CH₃)₂ | H |
| 49 | CH₃ | 2-CH(CH₃)₂ | 3-CH(CH₃)₂ |
| 50 | CH₃ | 2-CH(CH₃)₂ | 4-CH(CH₃)₂ |
| 51 | CH₃ | 2-CH(CH₃)₂ | 5-CH(CH₃)₂ |
| 52 | CH₃ | 2-CH(CH₃)₂ | 6-CH(CH₃)₂ |
| 53 | CH₃ | 3-CH(CH₃)₂ | 4-CH(CH₃)₂ |
| 54 | CH₃ | 3-CH(CH₃)₂ | 5-CH(CH₃)₂ |

The foregoing compounds can be present in pharmaceutical compositions comprising a compound described herein and a pharmaceutically acceptable carrier. In certain embodiments, the pharmaceutical composition further comprises a second therapeutic agent. In certain embodiments, the second therapeutic agent is a steroid, cyclosporine, vitamin D, vitamin D analog, keratolytic agent, topical retinoid, calcineurin inhibitor, or coal tar. A variety of different steroids, cyclosporines, vitamin D analogs, keratolytic agents, topical retinoids, calcineurin inhibitors, and coal tars are amenable to the present invention. In certain embodiments, the steroid is a topical steroid. Topical steroids can reduce plaque formation and have anti-inflammatory affects. Topical steroids may also modify the body's immune response to diverse stimuli. The topical steroid may, in certain embodiments, be a topical corticosteroid, such as triamcinolone acetonide (Artistocort, Kenalog) (0.1% cream) or betamethasone diproprionate (Diprolene, Diprosone) (0.05% cream). In certain embodiments, the second therapeutic agent is a cyclosporine, such as Cyclosporine A or a derivative of cyclosporine A. In certain embodiments, the second therapeutic agent is vitamin D or a vitamin D analog. Vitamin D analogs are sometimes used in patients with lesions resistant to older therapeutics or with lesions on the face or exposed areas where thinning of the skin would pose cosmetic problems. In certain embodiments, the vitamin D analog is calcipotriene. In certain embodiments, the second therapeutic agent is a keratolytic agent. Keratolytic agents can be used to remove scale, smooth the skin, and to treat hyperkeratosis in a subject. In certain embodiments, the keratolytic agent is anthralin, particularly anthralin 0.1-1% (Drithocreme, Anthra-Derm).

described in U.S. Pat. Nos. 4,894,366; 4,916,138; and 4,929,611; each of which is hereby incorporated by reference. Pimecrolimus is a macrolactam that has been reported to inhibit production of pro-inflammatory cytokines by T cells and mast cells. Pimecrolimus is described in U.S. Pat. No. 5,912,238, which is hereby incorporated by reference. Ascomycin is an ethyl analog of tacrolimus described by C. E. Griffiths in *Br. J. Dermatol.* 2001. April; 144(4):679-81. ISA247 is a cyclosporin derivative described in U.S. Pat. Nos. 6,605,593 and 6,613,739; each of which is hereby incorporated by reference.

In certain embodiments, the second therapeutic agent is a coal tar. Coal tar is an inexpensive treatment available over the counter in shampoos or lotions, and it is particularly useful in hair-bearing areas. One example of a coal tar is coal tar (DHS Tar, Doctar, Theraplex T)-antipruitic. In certain embodiments, the coal tar is present at a concentration of 2-10 percent by weight.

The benzodiazepinone compounds described above can be prepared based on the procedures depicted in Scheme 1.

Scheme 1.

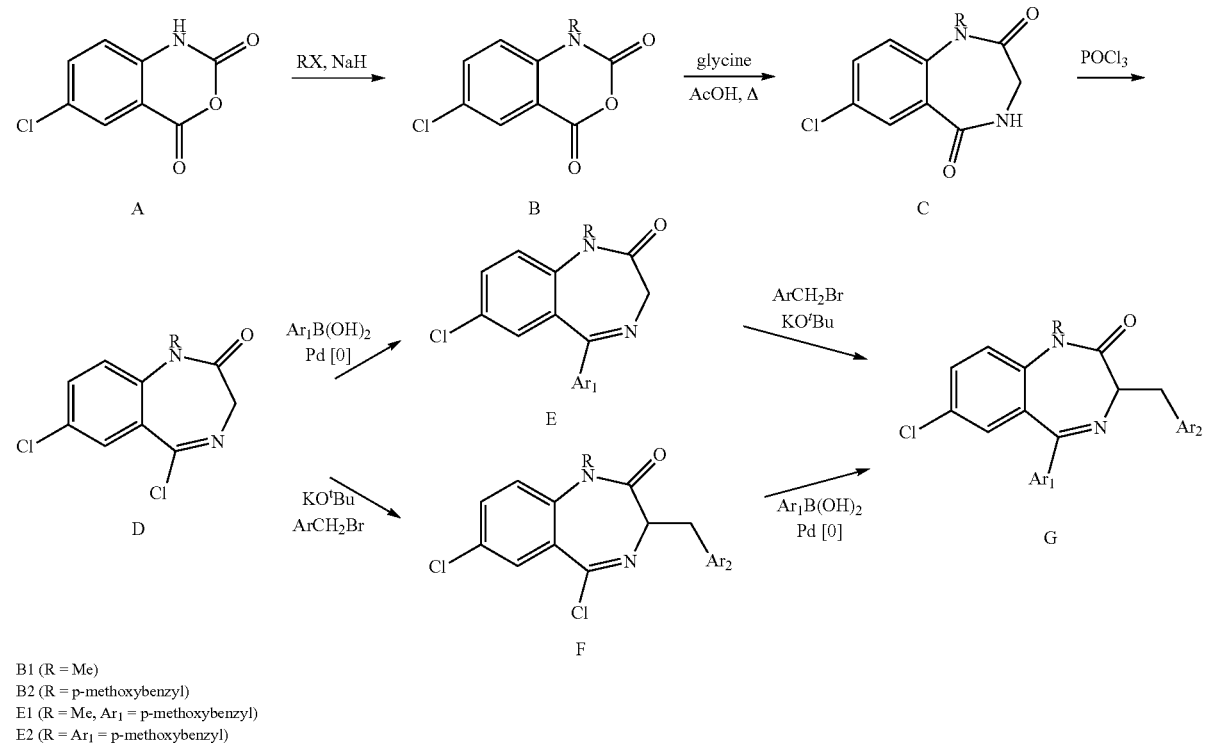

B1 (R = Me)
B2 (R = p-methoxybenzyl)
E1 (R = Me, Ar$_1$ = p-methoxybenzyl)
E2 (R = Ar$_1$ = p-methoxybenzyl)

In certain embodiments, the second therapeutic agent is a retinoid, such as a topical retinoid. Topical retinoids can decrease the cohesiveness of follicular epithelial cells and stimulate mitotic, resulting in an increase in turnover of follicular epithelial cells. In certain embodiments, the topical retinoid is tretinoin or tazarotene. In certain embodiments, the topical retinoid is tretinoin in the formulation marketed as Retin-A or Avita. In certain embodiments, the topical retinoid is tazarotene in the formulation marketed as Tazorac.

In certain embodiments, the second therapeutic agent is a calcineurin inhibitor, such as tacrolimus, pimecrolimus, ascomycin, or ISA247. Tacrolimus, also known as FK506, is N-alkylation of isatoic anhydride A can be carried out by treating compound A with sodium hydride and an alkyl or benzyl halide. Reaction of compound A with a benzyl halide, such as a p-methoxybenzyl halide, can be performed to install a protecting group, while reaction of compound A with various alkyl halides, e.g., methyl iodide or ethyl iodide, can be performed to install alkyl substitution on the N1-position of the benzodiazepine ring. Isatoic anhydride B can be converted to benzodiazepinone C upon reaction with glycine. See *Indian J. Chem. Sect. B.* 1985, 24, 905-907. This procedure provided benzodiazepinones C1 and C2 in good yield, which were subsequently treated with POCl$_3$ to provide imidoyl chlorides D1 or D2.

The "southern" aryl ring (substituent $Ar_1$) can be installed by Suzuki coupling of an aryl boronic acid, in accordance with procedures described by Nadin and co-workers. See *J. Org. Chem.* 2003, 68, 2844-2852. In particular, Suzuki coupling of imidoyl chlorides D1 and D2 with (4-methoxyphenyl)boronic acid afforded 5-arylbenzodiazepinones E1 and E2 in bulk quantities.

The "eastern" aryl ring (substituent $Ar_2$) can be installed by alkylation at the C3-position of the benzodiazepinone ring. Deprotonation at C-3 using a strong base, such as potassium tert-butoxide, following by the addition of a substituted benzyl halide provided benzodiazepinone G. The benzyl halides for this reaction can be obtained commercially or prepared from the corresponding benzyl alcohol using known procedures, such as treating a benzyl alcohol with thionyl chloride. A variety of benzyl alcohols are commercially available. In addition, a variety of benzyl alcohols can be prepared using any one of the following methods: i) reduction of a commercially available carboxylic acid (e.g., reduction using lithium aluminum hydride); ii) conversion of a dibromo-benzyl alcohol to a dialkyl-benzyl alcohol using, for example, a dialkylzinc reagent in the presence of a palladium catalyst, such as $PdCl_2(dppf)$; iii) conversion of a dibromobenzyl acetate to a dialkyl benzyl acetate followed by hydrolysis; iv) formylation of the appropriate aromatic compound followed by reduction; or v) conversion of a reactive chlorobenzoate ester to the respective alkyl benzoate ester using, for example, a Grignard reagent in the presence of an iron catalyst, such as $Fe(acac)_3$, followed by reduction.

Substituents on the "eastern" aromatic ring can be installed following C3-alkylation of the aromatic ring. For example, C3-alkylation with 3-bromobenzyl bromide, followed by Pd-catalyzed attachment of an alkyl group to the aromatic ring.

As illustrated in Scheme 1 above, benzodiazepinone G can also be prepared using a synthetic strategy involving C3-alkylation of imidoyl chloride D followed by a palladium-coupling reaction to install the "southern" aromatic ring. This synthetic strategy should be amenable to wide a variety of substrates, although aqueous work-ups of the C3-alkylation reaction should be performed quickly at low temperature to minimize any hydrolysis of the imidoyl chloride group. The aryl boronates used in this palladium-coupling reaction can be obtained from commercial sources or they can be easily prepared. For example, an aryl boronate can be prepared by treating an aryl bromide with bis(pinacolato)diboron in the presence of a palladium catalyst.

In situations where protecting groups are used during the synthesis, protecting groups on compound G can be removed using standard procedures known in the art. For example, the methoxy protecting group in $Ar_1$ can be removed using $AlCl_3$ to afford the p-hydroxyphenyl group. Similarly, N-deprotection of a p-methoxybenzyl group can be performed using cerium (IV) ammonium nitrate, according to literature procedures.

II. Therapeutic Applications of Benzodiazepinone Compounds

It is contemplated that the benzodiazepinone compounds of Formula I provide therapeutic benefits to patients suffering from various skin conditions. In one aspect, the invention provides a method of treating a skin condition, comprising administering a therapeutically effective amount of a compound of formula I to a subject in need thereof to ameliorate a symptom of the condition:

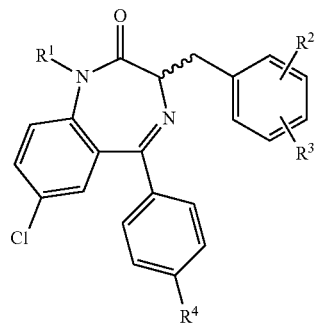

including salts, esters and prodrugs thereof, wherein $R^1$ is H or $C_{1-6}$ alkyl;

$R^2$ is H or $C_{1-6}$ alkyl;

$R^3$ is $C_{1-6}$ alkyl;

$R^4$ is hydroxyl or fluoro;

the stereochemical configuration at a stereocenter in a compound represented by formula I is R, S, or a mixture thereof; and provided that said compound is not

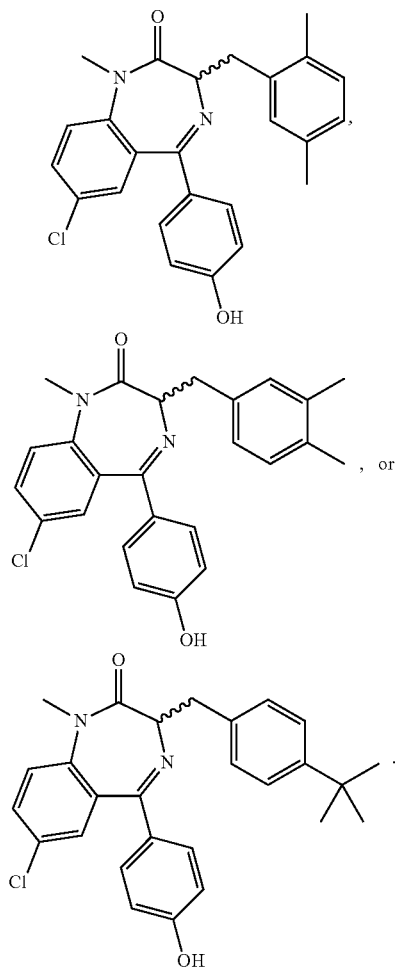

In certain embodiments, $R_4$ is fluoro. In certain other embodiments, the compound has the structure:

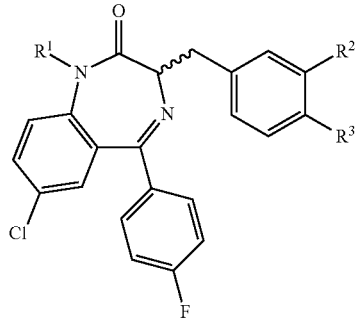

In certain other embodiments, $R_4$ is hydroxyl. In certain other embodiments, the compound has the structure:

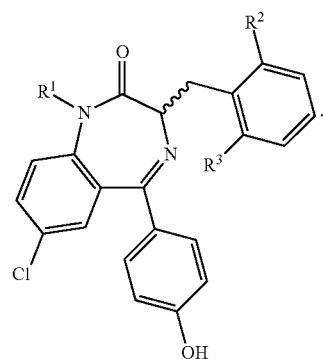

In certain other embodiments, the compound has the structure:

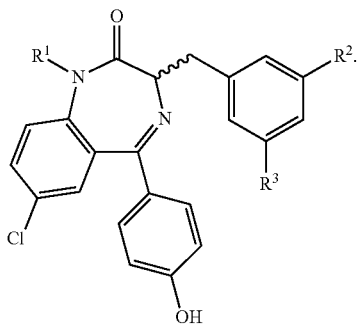

In certain other embodiments, $R^2$ and $R^3$ are $C_{1-3}$ alkyl. In certain other embodiments, $R^2$ and $R^3$ are methyl. In certain other embodiments, $R^2$ and $R^3$ are ethyl. In certain other embodiments, $R^2$ and $R^3$ are isopropyl. In certain other embodiments, $R^1$ is methyl. In certain other embodiments, $R^2$ is H, and $R^3$ is isopropyl. In certain other embodiments, $R^1$ is H or methyl; and $R^2$ and $R^3$ are $C_{1-3}$ alkyl. In certain other embodiments, the compound is:

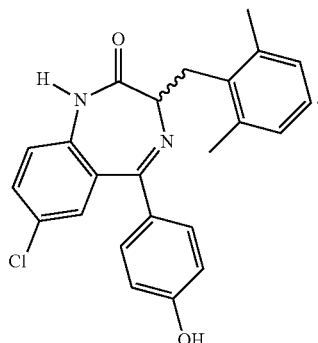

In certain other embodiments, the compound is:

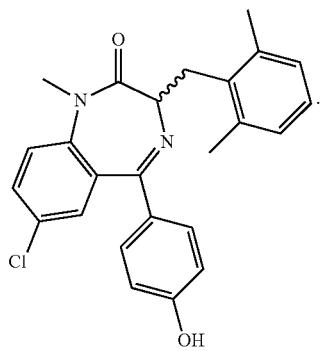 [SMILES: Cc1cccc(C)c1CC1N=C(c2ccc(O)cc2)c2cc(Cl)ccc2N(C)C1=O]

In certain other embodiments, the compound is one of the compounds listed in Tables 1 or 2. In certain other embodiments, the skin condition is associated with epidermal hyperplasia. In certain other embodiments, the skin condition is atopic dermatitis, rosacea or psoriasis. In certain other embodiments, the skin condition is psoriasis. There are a variety of forms of psoriasis, including plaque psoriasis, guttate psoriasis, nail psoriasis, inverse psoriasis, and scalp psoriasis. It is contemplated that one or more of these forms of psoriasis can be treated by administering a benzodiazepinone described herein.

In another aspect, the present invention provides a method of treating epidermal hyperplasia, comprising administering a therapeutically effective amount of a compound of formula I, described herein, to a subject in need thereof to ameliorate a symptom of the epidermal hyperplasia. In certain embodiments, the compound has the structure:

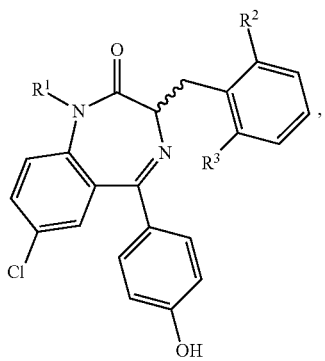

wherein $R^1$ is H or $C_{1-6}$ alkyl; $R^2$ is H or $C_{1-6}$ alkyl; $R^3$ is $C_{1-6}$ alkyl; and the stereochemical configuration at a stereocenter in the compound is R, S, or a mixture thereof.

In certain other embodiments, the compound has the structure:

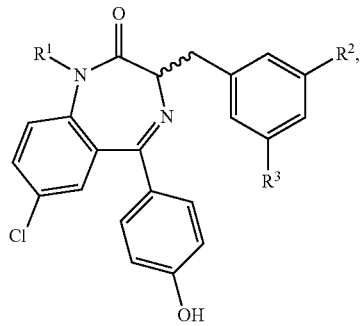

wherein $R^1$ is H or $C_{1-6}$ alkyl; $R^2$ is H or $C_{1-6}$ alkyl; $R^3$ is $C_{1-6}$ alkyl; and the stereochemical configuration at a stereocenter in the compound is R, S, or a mixture thereof.

In certain other embodiments, $R^2$ and $R^3$ are $C_{1-3}$ alkyl. In certain other embodiments, $R^2$ and $R^3$ are methyl. In certain other embodiments, $R^2$ and $R^3$ are ethyl. In certain other embodiments, $R^2$ and $R^3$ are isopropyl. In certain other embodiments, $R^1$ is methyl. In certain other embodiments, $R^2$ is H, and $R^3$ is isopropyl. In certain other embodiments, $R^1$ is H or methyl; and $R^2$ and $R^3$ are $C_{1-3}$ alkyl. In certain other embodiments, the compound is:

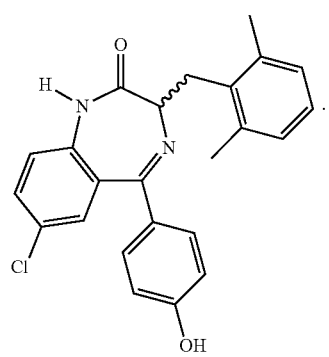 [SMILES: Cc1cccc(C)c1CC1N=C(c2ccc(O)cc2)c2cc(Cl)ccc2NC1=O]

In certain other embodiments, the compound is:

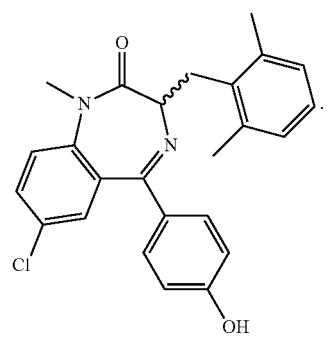 [SMILES: Cc1cccc(C)c1CC1N=C(c2ccc(O)cc2)c2cc(Cl)ccc2N(C)C1=O]

In certain other embodiments, the compound is one of the compounds listed in Tables 1 or 2.

In certain embodiments, the subject is a human. In certain other embodiments, the method further comprises administering to the subject a therapeutic agent selected from the group consisting of a steroid, cyclosporine, vitamin D, vitamin D analog, keratolytic agent, topical retinoid, calcineurin inhibitor, and coal tar. In certain embodiments, the steroid is a topical corticosteroid. In certain other embodiments, the topical corticosteroid is triamcinolone acetonide or betamethasone dipropionate; the vitamin D analog is calcipotriene; the keratolytic agent is anthralin; the topical retinoid is tretinoin or tazarotene; and the calcineurin inhibitor is tacrolimus, pimecrolimus, ascomycin, or ISA247. In certain other embodiments, the therapeutic agent is a steroid.

In another aspect, the present invention provides a method of reducing the proliferation of a keratinocyte cell, comprising exposing said cell to a compound of formula I, described herein. In certain embodiments, the compound has the structure:

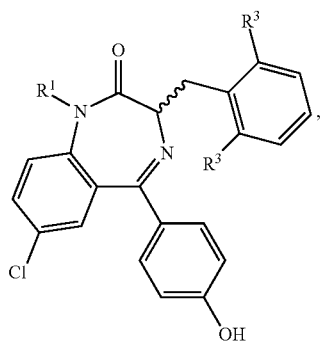

wherein $R^1$ is H or $C_{1-6}$ alkyl; $R^2$ is H or $C_{1-6}$ alkyl; $R^3$ is $C_{1-6}$ alkyl; and the stereochemical configuration at a stereocenter in the compound is R, S, or a mixture thereof.

In certain other embodiments, the compound has the structure:

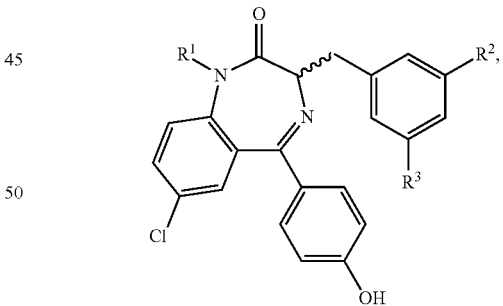

wherein $R^1$ is H or $C_{1-6}$ alkyl; $R^2$ is H or $C_{1-6}$ alkyl; $R^3$ is $C_{1-6}$ alkyl; and the stereochemical configuration at a stereocenter in the compound is R, S, or a mixture thereof.

In certain other embodiments, $R^2$ and $R^3$ are $C_{1-3}$ alkyl. In certain other embodiments, $R^2$ and $R^3$ are methyl. In certain other embodiments, $R^2$ and $R^3$ are ethyl. In certain other embodiments, $R^2$ and $R^3$ are isopropyl. In certain other embodiments, $R^1$ is methyl. In certain other embodiments, $R^2$ is H, and $R^3$ is isopropyl. In certain other embodiments, $R^1$ is H or methyl; and $R^2$ and $R^3$ are $C_{1-3}$ alkyl. In certain other embodiments, the compound is:

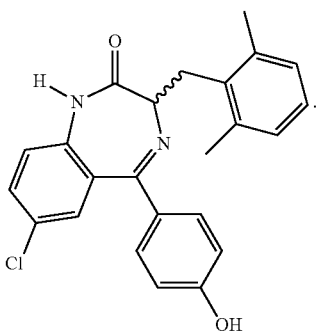 [SMILES: Cc1cccc(C)c1CC1N=C(c2ccc(O)cc2)c2cc(Cl)ccc2NC1=O]

In certain other embodiments, the compound is:

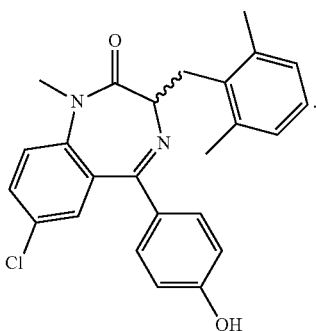 [SMILES: Cc1cccc(C)c1CC1N=C(c2ccc(O)cc2)c2cc(Cl)ccc2N(C)C1=O]

In certain other embodiments, the compound is one of the compounds listed in Tables 1 or 2.

In certain other embodiments, a method described herein further comprises, exposing said subject to ultraviolet radiation. Phototherapy has been shown to help treat psoriasis. There are two main forms of phototherapy, UVB and PUVA phototherapy. UVB, or Ultraviolet B, phototherapy uses light having a wavelength in the range of 290-320 nm. Such phototherapy is often combined with one or more topical treatments including: i) topically applying coal tar, followed by using UVB; ii) using a coal tar bath, followed by UVB, and then topically applying anthralin; or iii) using UVB in combination with topically applying corticosteroids, calcipotriene, tazarotene, or simply bland emollients. PUVA uses the photosensitizing drug methoxsalen (8-methoxypsoralens) in conjunction with UVA light (wavelengths in the 320-400 nm range). PUVA is thought to interfere with DNA synthesis (methoxsalen binds covalently to pyrimidine bases in DNA), decrease cellular proliferation, and induce apoptosis of cutaneous lymphocytes leading to localized immunosuppression.

III. Pharmaceutical Compositions, Formulations, and Exemplary Administration Routes and Dosing Considerations Exemplary embodiments of various contemplated medicaments and pharmaceutical compositions are provided below.

A. Preparing Medicaments

The compounds of the present invention are useful in the preparation of medicaments to treat or study a variety of skin conditions. In certain embodiments, the skin condition is associated with epidermal hyperplasia.

In addition, the compounds are also useful for preparing medicaments for treating or studying other skin conditions wherein the effectiveness of the compounds are known or predicted. The methods and techniques for preparing medicaments of a compound of the present invention are well-known in the art. Exemplary pharmaceutical formulations and routes of delivery are described below.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as discussed above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable for oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprise a mixture of at least one emulsifier with a fat or an oil or with both a fat and an oil.

Preferably, a hydrophilic emulsifier is included together with a lipophilic emulsifier so as to act as a stabilizer. In some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described above) of the present invention, e.g., encapsulation in liposomes, microparticles, microcapsules, receptor-mediated endocytosis, and the like. Methods of delivery include, but are not limited to, intra-arterial, intra-muscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To identify patients that can be beneficially treated, a tissue sample is removed from the patient and the cells are assayed for sensitivity to the agent.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or by oral administration, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

As described above, the invention includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. The determination of appropriate type and dosage of radiation treatment is also within the skill in the art or can be determined with relative ease.

The sensitizing function of the claimed compounds also addresses the problems associated with toxic effects of known therapeutics. In instances where the known agent is toxic, it is desirable to limit the dosages administered in all cases, and particularly in those cases where drug resistance has increased the requisite dosage. When the claimed compounds are co-administered with the known agent, they reduce the dosage required which, in turn, reduces the deleterious effects.

EXAMPLES

The invention, now being generally described, will be more readily understood by reference to the following examples, which are included merely for purposes of illustration of certain aspects and embodiments of the present invention, and are not intended to limit the invention.

Example 1

Representative Procedures for N-Alkylation of Isatoic Anhydrides

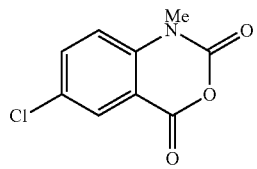 [SMILES: Cn1c(=O)oc(=O)c2cc(Cl)ccc21]

6-Chloro-1-methyl-1H-benzo[d][1,3]oxazine-2,4-dione (B1)

In a 3 L, 3-neck RBF equipped with mechanical stir, addition funnel, thermocouple and $N_2$ inlet, NaH (30.4 g) was suspended in anhydrous tetrahydrofuran (THF, 400 mL). While stirring at room temperature, a suspension of 5-chloroisotonic anhydride in THF (400 mL) was added in portionwise manner over 45 min. The reaction mixture was stirred for 50 min (reaction temperature went up from 18 to 28° C.). To this was added $CH_3I$ (285 g, 125 mL) over 15 min. The mixture was then stirred at 42° C. for 16 h. Because TLC showed that some unreacted starting material was still present in the reaction mixture, an additional 30 mL of $CH_3I$ was added and the reaction mixture stirred at 42° C. for an additional 3 h. Reaction mixture was cooled (RT) and quenched by the slow (40 min) addition of AcOH (55 mL). Reaction mixture was concentrated to give 275 g thick syrupy product, which was used without any further purification. $^1$H NMR (300 MHz, $CDCl_3$) δ 3.35 (s, 3H), 7.54 (d, 1H), 7.85 (d, 1H), 7.90 (s, 1H).

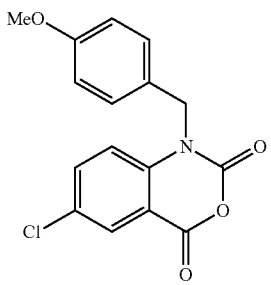 [SMILES: COc1ccc(Cn2c(=O)oc(=O)c3cc(Cl)ccc32)cc1]

6-Chloro-1-(4-methoxybenzyl)-1H-benzo[d][1,3]oxazine-2,4-dione (B2)

In a 3 L, 3-neck RBF equipped with mechanical stir, thermocouple and $N_2$ inlet, 90 g (0.455 mol) of 5-chloroisotonic anhydride was suspended in anhydrous THF (0.9 L). Under N₂, 4-methoxybenzylchloride (75 g, 0.48 mol) was added followed by the addition of tetrabutylammonium iodide (84 g, 0.23 mol). The reaction mixture was stirred for 5 min at room temperature and then 20 g (0.5 mol) of NaH was added portion-wise over 20 min (reaction temperature increased to 29° C. due to an exotherm and therefore reaction mixture was placed into a water bath to keep the temperature below 30° C.). Reaction was stirred for 16 h (RT). The next day, HPLC showed about 26% unreacted 5-chloroisotonic anhydride. Additional NaH (1 g) was added and the reaction mixture was heated to 32° C. and stirred for another 5 h. NMR showed that all of the starting material had been consumed. Reaction was quenched by adding 10 g of glacial acetic acid slowly, followed by stirring for 30 min. Reaction mixture was filtered through celite, and the filter cake was washed with THF. Filtrate was concentrated to give 280 g of crude product (yellow-brown solid), which was used with no further purification. $^1$H NMR (300 MHz, DMSO-$d_6$) δ 3.8 (s, 3H), 5.25 (s, 2H), 6.8 (d, 2H), 7.2 (m, 3H), 7.75 (d, 1H), 7.9 (d, 1H).

Example 2

Representative Procedures for Conversion of an Isatoic Anhydride to a Benzodiazepine-dione

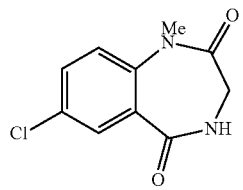 [SMILES: CN1C(=O)CNC(=O)c2cc(Cl)ccc21]

7-Chloro-1-methyl-3,4-dihydro-1H-benzo[e][1,4] diazepine-2,5-dione (C1)

In a 2 L RBF equipped with mechanical stir, condenser and N₂ inlet, glycine (38 g, 0.506 mol) was added to crude B1 (107 g, 0.506 mol) followed by the addition of AcOH (500 mL). Reaction flask was heated in a 130° C. oil bath for 7 h. Solvent was evaporated under suction with heating (50-60° C.). To the thick syrupy crude product was added 1 L of EtOAc followed by the slow addition of aqueous NaHCO₃ (saturated) to adjust the pH to ~7. Then 10 mL of 2 M NaOH was added to adjust the pH to ~9-10. The mixture gave a solid along with organic and aqueous layers. The solid was filtered to give product containing some impurity. The solid was partitioned between 400 mL dichloromethane (DCM) and 200 mL NaHCO₃, and the resultant slurry was stirred for 20 min, then filtered to remove an insoluble impurity. The DCM layer was separated and washed with 3% NaHCO₃ and then brine (200 mL). The DCM layer was dried (MgSO₄), filtered and concentrated to give 50 g of pure product. EtOAc layer was concentrated to give 67 g of solid product with some impurity. The aqueous layer was extracted with EtOAc (2×400 mL). Combined organics were dried over Na₂SO₄, filtered and concentrated to give an additional 6.7 g of crude product. Total of 123.4 g of product was obtained, 50 g of which was very clean (yield quantitative). $^1$H NMR (300 MHz, CDCl₃) δ 3.2 (s, 3H), 3.5 (m, 1H), 3.8 (m, 1H), 7.35 (d, 1H), 7.6 (m, 2H), 8.8 (t, 1H).

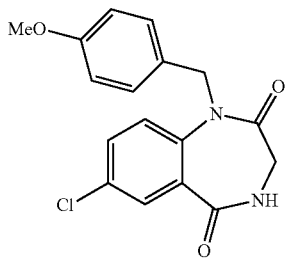 [SMILES: COc1ccc(CN2C(=O)CNC(=O)c3cc(Cl)ccc32)cc1]

7-Chloro-1-(4-methoxybenzyl)-3,4-dihydro-1H-benzo[e][1,4]diazepine-2,5-dione (C2)

In a 2 L RBF equipped with mechanical stir, condenser and N₂ inlet, glycine (34 g, 0.45 mol) was added to B2 (280 g) followed by the addition of AcOH (500 mL). Reaction flask was heated in a 130° C. oil bath for 8 h. Solvent was removed on the rotary evaporator at 50-60° C. To the thick syrupy crude product was added heptane (1 L) and H₂O (1 L) followed by the addition of NaHCO₃ to adjust the pH to ~8-9. The mixture gave a solid along with organic and aqueous layers. The organic and aqueous layers were decanted and the solid was slurried with 500 mL of 5% NaHCO₃ solution. NaHCO₃ layer was decant and sticky solid was suspended in 700 mL ethylacetate (EtOAc) and 300 mL of dichloromethane (DCM). The mixture was stirred for 20 min, filtered and the filter cake was washed with 1 L of DCM. The filtrate was concentrated and residue was pass through 330 g silica gel plug using 25/75 to 75/25 EtOAc/heptane (total of 8 L). Clean fractions were combined to give 58 g of pure product. An additional 13 g of ~70% pure product was obtained from less pure fractions. Yield was 47% over two steps. $^1$H NMR (300 MHz, DMSO-$d_6$) δ 3.45 (m, 1H), 3.6 (s, 3H), 3.8 (m, 1H), 4.8 (d, 1H), 5.3 (d, 1H), 6.8 (d, 2H), 7.1 (d, 2H), 7.7-7.5 (m, 3H), 8.9 (t, 1H).

Example 3

Representative Procedures for Synthesis of an Imidoyl Chloride

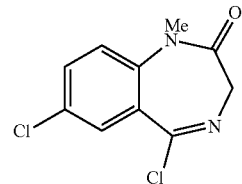 [SMILES: CN1C(=O)CN=C(Cl)c2cc(Cl)ccc21]

(E)-5,7-Dichloro-1-methyl-1H-benzo[e][1,4]diazepin-2(3H)-one (D1)

In a 1 L 2-neck RBF equipped with mechanical stir, condenser and N₂ inlet, C1 (42.5 g, 0.189 mol) was suspended into 400 mL of toluene. To this was added N,N-dimethylanaline (45.5 g. 0.375 mol) followed by the addition of POCl₃ (29 g, 0.189 mol) and the reaction mixture stirred for 3 minutes at room temperature (RT). Reaction flask was placed in a 90° C. oil bath and the reaction mixture stirred/heated for 7 h and then at RT for 9 h. The reaction was quenched by adding 500 mL of ice water and stirred for 15 min. Organic layer was separated and quickly washed with cold 0.5 M HCl (300 mL), cold water (300 mL), and then cold saturated NaHCO$_3$ (300 mL). Organic layer was dried (MgSO$_4$), filtered and concentrated on a rotary evaporator to give 40 g of yellow solid. Yield 87.5%. $^1$H NMR (300 MHz, DMSO-d$_6$) δ 3.25 (s, 3H), 3.8-3.9 (s, 1H, br), 4.3-4.4 (s, 1H, br), 7.4 (d, 1H), 7.7-7.8 (m, 2H).

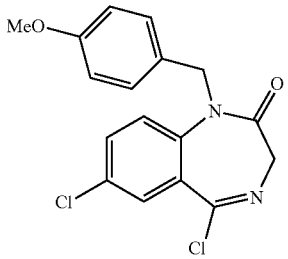 [SMILES: COc1ccc(CN2C(=O)CN=C(Cl)c3cc(Cl)ccc32)cc1]

(E)-5,7-Dichloro-1-(4-methoxybenzyl)-1H-benzo[e][1,4]diazepin-2(3H)-one

In a 1 L 3-neck RBF equipped with magnetic stir bar, condenser and N$_2$ inlet, C2 (45 g, 0.136 mol) was suspended in 400 mL of toluene. To this was added N,N-dimethylanaline (33 g, 0.272 mol) followed by the addition of POCl$_3$ (23 g) and the reaction stirred for 3 min (RT). Reaction flask was placed into a 90° C. oil bath and the reaction mixture was heated for 5 h and then cooled. The reaction was quenched by adding 450 mL of ice water and stirred for 15 min. Organic layer was separated and quickly washed with cold water (2×250 mL) and brine (300 mL). Organic layer was dried over MgSO$_4$, filtered and concentrated on a rotary evaporator to give 57 g of black crude product. Crude product was used for next step with no further purification. Yield 87.5%.

Example 4

Representative Procedures for the Preparation of Benzyl Halides

Benzyl halides can prepared from the corresponding benzyl alcohol using known procedures, such as by treating a benzyl alcohol with thionyl chloride. A variety of benzyl alcohols are commercially available. In addition, a variety of benzyl alcohols can be prepared using the following methods: i) reduction of a commercially available carboxylic acid (e.g., reduction using lithium aluminum hydride); ii) conversion of a dibromo-benzyl alcohol to a dialkyl-benzyl alcohol using, for example, a dialkylzinc reagent in the presence of a palladium catalyst, such as PdCl$_2$(dppf); iii) conversion of a dibromobenzyl acetate to a dialkyl benzyl acetate followed by hydrolysis; iv) formylation of the appropriate aromatic followed by reduction; or v) conversion of a reactive chlorobenzoate ester to the respective alkyl benzoate ester using, for example, a Grignard reagent in the presence of an iron catalyst, such as Fe(acac)$_3$, followed by reduction.

Part I: Representative Procedures for the Preparation of a Substituted Benzyl Alcohol from Dibromotoluene 1,3-Dibromo-2-(bromomethyl)benzene A mixture of 2,6-dibromotoluene (22.9 g, 92 mmol), N-bromosuccinimide (NBS) (15 g, 84 mmol), CCl$_4$ (250 mL) and benzoyl peroxide (0.03 eq) was stirred at 85° C. (hot oil bath temperature) for 16 h, cooled to RT, filtered, washed with aq. NaHSO$_3$, dried (Na$_2$SO$_4$), filtered, and evaporated to give 29.5 g (yield of 98%) of title product as a white solid. This solid contained 10% unreacted starting material but was successfully used without further purification. $^1$H NMR (300 MHz, CDCl$_3$) δ 4.81 (s, 2H), 7.01 (t, 1H), 7.53 (d, 2H).

2,6-Dibromobenzyl acetate

A mixture of 1,3-dibromo-2-(bromomethyl)benzene (27.6 g, 84 mmol), NaOAc (35.5 g, 5 eq.) and dimethylformamide (DMF) (150 mL) was stirred at 100° C. (hot oil bath temperature) for 1.75 h, allowed to cool, and then partitioned between heptane (500 mL) and water (200 mL). After removing the organic layer, the aqueous layer was extracted with heptane (200 mL). The combined organics were washed with H$_2$O (2×300 mL), dried (Na$_2$SO$_4$), filtered, and evaporated to give 24.57 g (yield of 95%) of title product as a colorless oil. This oil contained 13% unreacted starting material but was successfully used without further purification. $^1$H NMR (300 MHz, CDCl$_3$) δ 2.10 (s, 3H), 5.41 (s, 2H), 7.08 (t, 1H), 7.58 (d, 2H).

2,6-Diethylbenzyl acetate

To a cooled (dry ice-acetone bath) mixture of 2,6-dibromobenzyl acetate (5.05 g, 16.4 mmol) and PdCl$_2$(dppf) (0.08 eq) in dry THF (50 mL) was added 1.1 M Et$_2$Zn (60 mL, 66 mmol, 4 eq). The resulting mixture was allowed to warm to RT, stirred at 45° C. (programmed block temperature, ~40 h), and added to a stirred mixture of dilute HCl and heptane/EtOAc. The organic layer was dried (Na$_2$SO$_4$), filtered, and evaporated. Chromatography (2%-10% EtOAc/heptane stepwise gradient) gave 2.12 g (yield of 63%) of the title product, along with 0.20 g of 2,6-diethylbenzyl alcohol. $^1$H NMR (300 MHz, CDCl$_3$) δ 1.21 (t, 6H), 2.07 (s, 3H), 2.70 (q, 4H), 5.19 (s, 2H), 7.09 (d, 2H), 7.22 (dd, 1H). The following compound was prepared by making appropriate substitutions to the above procedure:

2,6-dimethylbenzyl acetate $^1$H NMR (300 MHz, CDCl$_3$) δ 2.06 (s, 3H), 2.39 (s, 6H), 5.17 (s, 2H), 7.02 (d, 2H), 7.12 (dd, 1H).

(2,6-Diethylphenyl)methanol

A mixture of 2,6-diethylbenzyl acetate (2.11 g, 10.2 mmol), MeOH (20 mL), H$_2$O (6 mL), and NaOH (1.99 g, 50 mmol, 5 eq) was stirred at RT overnight. After concentrating, the mixture was extracted with heptane (50 mL). The organic layer was dried (Na$_2$SO$_4$), filtered, and evaporated to give 1.90 g of title product. $^1$H NMR (300 MHz, CDCl$_3$) δ 1.23 (t, 1H, OH), 1.24 (t, 6H), 1.37 (br s, 1H), 2.79 (q, 4H), 4.75 (d, 2H), 7.09 (d, 2H), 7.21 (dd, 1H). The following compound was prepared by making appropriate substitutions to the above procedure: (2,6-Dimethylphenyl)methanol. $^1$H NMR (300 MHz, CDCl$_3$) δ 1.25 (t, 1H, OH), 2.41 (s, 6H), 4.72 (d, 2H), 7.0-7.15 (m, 3H).

Part 2: Representative Procedure for the Synthesis of an Alkyl-Substituted Benzoate Ester from a Halo-Substituted Benzoate Ester Methyl 2,4-diethylbenzoate To a mixture of Fe(acac)$_3$ (0.34 g, 0.96 mmol), methyl 2,4-dichlorobenzoate (4.0 g, 19.6 mmol), and N-methyl-2- pyrrolidinone (8 mL) in THF (100 mL) at −20° C. under nitrogen was added a tetrahydrofuran (THF) solution (1.0 M) of ethylmagnesium bromide (40.0 mL, 40.0 mmol) over a period of ~5 min. The resulting mixture was stirred while gradually warming to ambient temperature. Stirring was continued for an additional 17 h. The reaction mixture was partitioned between water and dichloromethane. The organic layer was separated, washed with brine, dried (MgSO4), and pumped to dryness under reduced pressure. The brown residue was purified by column chromatography (SiO2, 20% EtOAc/heptane) to give 1.2 g of the desired product as a clear oil (yield of 32%), along with 1.1 g of methyl 4-ethylbenzoate. $^1$H NMR (300 MHz, DMSO-d$_6$) δ 1.15 (t, 3H), 1.20 (t, 3H), 2.66 (q, 2H), 2.92 (q, 2H), 3.82 (s, 3H), 7.15 (d, 1H), 7.23 (s, 1H), 7.76 (d, 1H).

Part 3: Representative Procedure for the Synthesis of an Alkyl-Substituted Benzaldehyde from Alkyl-Substituted Benzene 2,5-Diisopropylbenzaldehyde In a 200 mL single neck RBF, equipped with magnetic stir bar, 1,4-diisopropylbenzene (4 g, 25 mmol) was dissolved into 50 mL of chloroform. To this solution was added SnCl$_4$ (11.5 g, 5.2 mL, 4.5 mmol) via syringe over 5 min. The reaction mixture was stirred for 5 min and then Cl$_2$CHOMe (2.8 g, 24 mmol) was added via syringe over 15 min. The reaction mixture was stirred for 20 h (RT) and reaction progress was followed by GC/MS. Reaction was quenched by adding 70 mL of water and stirring the mixture for 10 min. Organic layer was separated and washed with 3 N HCl (2×50 mL). The organic layer was dried over MgSO$_4$, filtered and concentrated to give 4 g of crude product. This was subjected to column chromatography using 80 g of silica and from 100% heptane to 95:5 Heptane:EtOAc as a mobile phase to give 2.4 g of product (yield of 56%). $^1$H NMR (300 MHz, CDCl$_3$) δ 1.17 (d, 6H), 1.25 (d, 6H), 2.9 (septet, 1H), 4.9 (septet, 1H), 7.4 (m, 2H), 7.65 (d, 1H), 10.35 (s, 1H).

The following compound was prepared based on the above procedure: 3,4-Diethylbenzaldehyde. $^1$H NMR (300 MHz, DMSO-d$_6$) δ 1.21 (m, 6H), 2.72 (q, 4H), 7.41 (d, 1H), 7.71 (d, 1H), 7.75 (s, 1H).

Part 4: Representative Procedure for the Synthesis of an Alkyl-Substituted Benzyl Alcohol from an Alkyl-Substituted Benzaldehyde (2,5-Diisopropylphenyl)methanol In a 2-neck RBF equipped with magnetic stir bar and N$_2$ inlet, 2,5-diisopropylbenzaldehyde (1.7 g, 9 mmol) was dissolved into 30 mL of EtOH and NaBH$_4$ (0.37 g, 10 mmol) was added over 20 min (portion-wise). After 18 h stirring at RT, ~95% of solvent was removed on a rotary evaporator and then 5 mL of 0.5 M HCl was added and product was extracted with 25 mL of EtOAc. Organic layer was washed with 15 mL of H$_2$O and 15 mL of brine, dried over Na$_2$SO$_4$, filtered and concentrated to dryness to obtain crude product. This material was subjected to chromatography using heptane: EtOAc as mobile phase to provide 1.1 g of pure product. Yield 65%. $^1$H NMR (300 MHz, CDCl$_3$) δ 1.2-1.3 (d, 12H), 2.8 (septet, 1H), 3.2 (septet, 1H), 5.7 (s, 2H), 7.1-7.3 (m, 3H).

Part 5: Representative Procedure for the Synthesis of an Alkyl-Substituted Benzyl Alcohol from a Dibromobenzyl Alcohol (3,5-Diethylphenyl)methanol To a cooled (dry ice) mixture of 3,5-dibromobenzyl alcohol (1 g, 3.8 mmol) and PdCl$_2$(dppf) [0.07 eq] in dry THF (10 mL) was added 1.1 M Et$_2$Zn (15 mL, 16 mmol, 4.4 eq). The resulting mixture was allowed to warm to RT, stirred at 45° C. (programmed block temperature, overnight). To bring the reaction to completion (disappearance of both starting material and monoalkylated product) additional 1.1 M Et$_2$Zn (10 mL, 11 mmol, 2.9 eq) was added with continued stirring at 45° C. (again overnight). After cooling, the reaction mixture was then added to a stirred mixture of dilute HCl and heptane/EtOAc (2:1; ~200 mL), and the organic layer was dried (Na$_2$SO$_4$), filtered, and evaporated. Chromatography (10% EtOAc/heptane) gave 0.33 g (yield of 53%) of title product. $^1$H NMR (300 MHz, CDCl$_3$) δ 1.22 (t, 6H), 1.65 (br s, 1H), 2.61 (q, 4H), 4.66 (s, 2H), 6.95-7.05 (m, 3H).

The following compounds were prepared by making the appropriate substitutions to the above procedure.

(2,5-Diethylphenyl)methanol $^1$H NMR (300 MHz, CDCl$_3$) δ 1.22 (t, 6H), 1.50 (br s, 1H), 2.61 (q, 2H), 2.65 (q, 2H), 4.70 (br s, 1H), 7.0-7.2 (m, 3H).

(3,4-Diethylphenyl)methanol $^1$H NMR (300 MHz, DMSO-d$_6$) δ 1.14 (t, 3H), 1.20 (t, 3H), 2.62-2.70 (m, 4H), 4.46 (d, 2H), 5.03 (t, 1H), 7.05-7.13 (m, 3H).

Part 6: Representative Procedure for the Synthesis of an Alkyl-Substituted Benzyl Alcohol from an Alkyl-Substituted Benzyl Ester (2,4-Diethylphenyl)methanol To a suspension of lithium aluminum hydride (0.47 g, 11.8 mmol) in anhydrous THF (20 mL) at room temperature under nitrogen was added a solution of methyl 2,4-diethylbenzoate (1.5 g, 7.8 mmol) in THF (15 mL) with stirring over a period of ~5 min. The resulting mixture was stirred at room temperature for 60 min and was then quenched by slow addition of ethyl acetate (until bubbling stopped). The mixture was partitioned between ethyl acetate and 1N HCl (aq). The aqueous layer was separated and extracted with ethyl acetate. Organic layers were combined, dried (MgSO4), and evaporated to dryness to give 1.3 g of the desired alcohol as a clear oil (yield of 100%). $^1$H NMR (300 MHz, CDCl$_3$) δ 1.13 (t, 3H), 1.17 (t, 3H), 2.58 (q, 2H), 2.61 (q, 2H), 4.43 (d, 2H), 5.02 (t, 1H), 7.05-7.11 (m, 3H).

Part 7: Representative Procedure for the Synthesis of an Alkyl-Substituted Benzylhalide from an Alkyl-Substituted Benzyl Alcohol 2-(Chloromethyl)-1,3-diethylbenzene To a mixture of (2,6-diethylphenyl)methanol (1.83 g, 11.1 mmol), toluene (20 mL) and DMF (6 drops) was added SOCl$_2$ (2.1 g, 1.6 eq). The resulting solution was stirred at RT (1 h). After evaporating to dryness, the residue was taken up in heptane (~50 mL) and washed with water (~5 mL), dried ($Na_2SO_4$), filtered and evaporated to give 1.97 g (yield of 97%) of title product. $^1$H NMR (300 MHz, $CDCl_3$) δ 1.28 (t, 6H), 2.79 (q, 2H), 4.70 (s, 2H), 7.09 (d, 2H), 7.20 (m, 1H).

The following compounds were prepared by making the appropriate substitutions to the above procedure.

1-(Chloromethyl)-2,3-dimethylbenzene $^1$H NMR (300 MHz, $CDCl_3$) δ 2.29 (s, 3H), 2.31 (s, 3H), 4.60 (s, 2H), 7.0-7.2 (m, 3H).

1-(Iodomethyl)-2,4-dimethyl benzene $^1$H NMR (300 MHz, $CDCl_3$) δ 2.23 (s, 6H), 4.35 (s, 2H), 6.9-7.05 (m, 2H), 7.1 (d, 1H).

1-(Chloromethyl)-3,4-dimethyl benzene $^1$H NMR (300 MHz, $CDCl_3$) δ 2.20 (s, 6H), 4.67 (s, 2H), 7.1-7.2 (m, 3H).

2-(Chloromethyl)-1,3-dimethylbenzene $^1$H NMR (300 MHz, $CDCl_3$) δ 2.42 (s, 6H), 4.64 (s, 2H), 7.02 (d, 2H), 7.12 (dd, 1H).

2-(Iodomethyl)-1,4-dimethyl benzene $^1$H NMR (300 MHz, $CDCl_3$) δ 2.22 (s, 3H), 2.26 (s, 3H), 4.15 (s, 2H), 6.9-7 (m, 2H), 7.16 (d, 1H).

1-(Chloromethyl)-2-ethylbenzene $^1$H NMR (300 MHz, $CDCl_3$) δ 1.2-1.3 (t, 3H), 2.75 (q, 2H), 4.55 (s, 2H), 7.1-7.35 (m, 4H).

1-(Chloromethyl)-2,4-diethylbenzene $^1$H NMR (300 MHz, $CDCl_3$) δ 1.27 (m, 6H), 2.69 (q, 2H), 2.78 (q, 2H), 4.66 (s, 2H), 6.98-7.10 (m, 2H), 7.26 (m, 1H, contains chloroform signal).

1-(Chloromethyl)-3,4-diethylbenzene $^1$H NMR (300 MHz, DMSO-$d_6$) δ 1.21 (t, 3H), 1.25 (t, 3H), 2.60 (q, 2H), 2.64 (q, 2H), 4.71 (s, 2H), 7.15-7.40 (m, 3H).

1-(Chloromethyl)-3,5-diethylbenzene $^1$H NMR (300 MHz, $CDCl_3$) δ 1.23 (t, 6H), 2.63 (q, 4H), 4.54 (s, 2H), 7.01 (d, 2H), 7.05 (d, 1H).

2-(Chloromethyl)-1,4-diethylbenzene $^1$H NMR (300 MHz, $CDCl_3$) δ 1.22 (t, 3H), 1.26 (t, 3H), 2.61 (q, 2H), 2.84 (q, 2H), 4.60 (s, 2H), 7.0-7.2 (m, 3H).

2-(Bromomethyl)-1,4-diisopropylbenzene $^1$H NMR (300 MHz, $CDCl_3$) δ 1.1-1.2 (d, 6H), 1.2-1.3 (d, 6H), 2.8 (septet, 1H), 3.25 (septet, 1H), 4.55 (s, 2H), 7.1-7.3 (m, 3H).

1-(Chloromethyl)-4-ethylbenzene and 1-(Chloromethyl)-4-isopropylbenzene.

Example 5

Representative Procedures for the Synthesis of Benzo[e][1,4]diazepin-2(3H)-ones from Imidoyl Chlorides Part I: Palladium-Coupling Reaction (Z)-7-Chloro-5-(4-methoxyphenyl)-1-methyl-1H-benzo[e][1,4]diazepin-2(3H)-one (E1)

In a 1 L 3-neck RBF equipped with magnetic stir bar, condenser, thermocouple, and $N_2$ inlet, crude D1 (30 g, 0.124 mol) was dissolved into 300 mL of ethylene glycol dimethyl ether (DME). To this was added a solution of $Na_2CO_3$ (21 g, 0.2 mol in 200 mL of $H_2O$) followed by addition of 4-methoxyphenyl boronic acid (22 g, 0.145 mol) and Pd(PPh$_3$)$_4$ (1.2 g, 8.3 mmol). The reaction mixture was heated in a 85° C. oil bath, under $N_2$, for 2 h and then cool to room temp. To this was added 200 mL of EtOAc and the mixture stirred for 5 min. The organic layer was separated and washed with $H_2O$ (200 mL) and brine (200 mL). The organic layer was dried over $MgSO_4$ and then concentrated to dryness to give 53 g of crude product. This material was subjected to silica gel chromatography using 210 g of silica gel and EtOAc/hepatene (12:88 to 30:70 to 50:50 to 70:30; total of 8 L mobile phase). Fractions containing pure product were combined and concentrated to dryness to give 42.7 g of pure product in approximately quantitative yield. $^1$H NMR (300 MHz, $CDCl_3$) δ 3.38 (s, 3H), 3.73 (d, 1H), 3.85 (s, 3H), 4.75 (d, 1H), 6.9 (m, 2H), 7.31 (m, 2H), 7.48-7.58 (m, 3H).

(Z)-7-Chloro-1-(4-methoxybenzyl)-5-(4-methoxyphenyl)-1H-benzo[e][1,4]diazepin-2(3H)-one (E2)

In a 1 L 3-neck RBF equipped with magnetic stir bar, condenser, thermocouple, and $N_2$ inlet, crude D2 (54 g) was dissolved into 360 mL of DME. To this was added a solution of $Na_2CO_3$ (23 g, 0.15 mol, in 250 mL of $H_2O$) followed by the addition of 4-methoxyphenyl boronic acid (22.7 g, 0.15 mol) and Pd(PPh$_3$)$_4$ (1.4 g, 1.2 mmol). The reaction mixture was heated in a 85° C. oil bath for 2 h and then cooled (RT). To this was added 200 mL of EtOAc and the mixture was stirred for 5 min. The organic layer was separated and washed with 200 mL $H_2O$ and then brine. The organic layer was concentrated to dryness to give 68 g of crude product. This material was subjected to column chromatography using 550 g of silica gel and 25/75 to 60/40 EtOAc/heptane. Fractions containing pure product were combined to give 21 g of pure product, and other fractions containing a small amount of impurity (by TLC) gave another 20 g of product. $^1$H NMR spectra of both lots appeared identical. A total of 41 g of product was obtained, providing the product in 72% yield over two steps. $^1$H NMR (300 MHz, $CDCl_3$) δ 3.7 (s, 3H), 3.80 (d, 1H), 3.85 (s, 3H), 4.57 (d, 1H), 4.85 (d, 1H), 5.57 (d, 1H), 6.63 (d, 2H), 6.85-6.95 (m, 4H), 7.16 (d, 1H), 7.3-7.44 (m, 4H).

Part II: C3-Alkylation of Benzo[e][1,4]diazepin-2(3H)-ones (Z)-7-Chloro-5-(4-methoxyphenyl)-1-methyl-3-(2-methylbenzyl)-1H-benzo[e][1,4]diazepin-2(3H)-one To a stirred and cooled (dry ice/acetone bath) solution of E1 (0.50 g, 1.59 mmol) in THF (8 mL) was slowly added 1 M KO$^t$Bu (2.4 mL, 2.4 mmol, 1.5 eq). The resulting deep red mixture was stirred over dry ice/acetone bath ~10 min followed by the slow addition of a solution of 2-methylbenzyl bromide (0.46 g, 2.5 mmol, 1.5 eq) in THF (2 mL). After stirring another ~35 min at −78° C., the reaction mixture was quenched with water and diluted with EtOAc. The organic layer was dried ($Na_2SO_4$), filtered and evaporated (rotovap, then high vacuum). Chromatography over silica gel using 20-40% EtOAc/heptane gave 0.56 g (yield of 84%) of the title product. Noting that, when using benzyl chlorides as alkylating agents, tetrabutyl ammonium iodide was added along with the alkylating agent at the low temperature. $^1$H NMR (300 MHz, $CDCl_3$) δ 2.38 (s, 3H), 3.41 (s, 3H), 3.5-3.65 (m, 2H), 3.74 (dd, 1H), 3.84 (s, 3H), 6.89 (dt, 2H), 7.05-7.15 (m, 3H), 7.25-7.35 (m, 3H), 7.45-7.5 (m, 3H).

The following compounds were prepared by making the appropriate substitutions to the above procedures.

(Z)-7-Chloro-5-(4-methoxyphenyl)-3-(3-bromobenzyl)-1-methyl-1H-benzo[e][1,4]diazepin-2(3H)-one $^1$H NMR (300 MHz, $CDCl_3$) δ 3.40 (s, 3H), 3.45-3.55 (m, 2H), 3.67 (dd, 1H), 3.86 (s, 3H), 6.91 (d, 2H), 7.14 (t, 1H), 7.25-7.3 (m, 3H), 7.33 (ddd, 1H), 7.45-7.55 (m, 4H).

(Z)-7-Chloro-5-(4-methoxyphenyl)-3-(3-methylbenzyl)-1-methyl-1H-benzo[e][1,4]diazepin-2(3H)-one $^1$H NMR (300 MHz, $CDCl_3$) δ 2.31 (s, 3H), 3.38 (s, 3H), 3.5-3.6 (m, 2H), 3.68 (dd, 1H), 3.82 (s, 3H), 6.88 (d, 2H), 6.99 (m, 1H), 7.1-7.2 (m, 3H), 7.2-7.3 (m, 3H+$CHCl_3$), 7.4-7.53 (m, 3H).

(Z)-7-Chloro-3-(2,6-dimethylbenzyl)-5-(4-methoxyphenyl)-1-methyl-1H-benzo[e][1,4]diazepin-2(3H)-one $^1$H NMR (300 MHz, $CDCl_3$) δ 2.39 (s, 6H), 3.40 (dd, 1H), 3.41 (s, 3H), 3.72 (dd, 1H), 3.82 (s, 3H), 3.87 (dd, 1H), 6.87 (d, 2H), 6.98-7.04 (m, 2H), 7.22 (fine d, 1H), 7.28 (d, 1H), 7.39 (d, 2H), 7.48 (dd, 1H).

(Z)-7-Chloro-3-(3,5-dimethylbenzyl)-5-(4-methoxyphenyl)-1-methyl-1H-benzo[e][1,4]diazepin-2(3H)-one $^1$H NMR (300 MHz, $CDCl_3$) δ 2.28 (s, 6H), 3.39 (s, 3H), 3.47 (m, 2H), 3.65 (m, 1H), 3.85 (s, 3H), 6.82 (s, 1H), 6.89 (m, 2H), 6.97 (s, 2H), 7.26 (m, 2H), 7.47 (m, 3H).

(Z)-3-(2,6-Diethylbenzyl)-7-chloro-5-(4-methoxyphenyl)-1-methyl-1H-benzo[e][1,4]diazepin-2(3H)-one $^1$H NMR (300 MHz, $CDCl_3$) δ 1.13 (t, 6H), 2.65-2.8 (m, 2H), 2.8-2.95 (m, 2H), 3.43 (s, 3H), 3.49 (dd, 1H), 3.68 (dd, 1H), 3.8-3.95 (m, 4H, includes singlet for OMe at 3.84), 6.87 (d, 2H), 7.04 (dd, 2H), 7.13 (dd, 1H), 7.20 (fine d, 1H), 7.28 (d, 1H), 7.40 (d, 2H), 7.47 (dd, 1H).

(Z)-3-(3,4-Diethylbenzyl)-7-chloro-5-(4-methoxyphenyl)-1-methyl-1H-benzo[e][1,4]diazepin-2(3H)-one $^1$H NMR (300 MHz, DMSO-$d_6$) δ 1.12 (m, 6H), 2.45-2.75 (m, 4H; contains DMSO signal), 3.3-3.45 (m, 2H; contains benzylic protons, N-Me, and $H_2O$ signals), 3.69 (m, 1H), 3.81 (s, 3H), 6.99 (m, 3H), 7.09 (m, 1H), 7.21 (s, 2H), 7.48 (d, 2H), 7.62 (d, 1H), 7.70 (fine dd, 1H).

(Z)-3-(3,5-Diethylbenzyl)-7-chloro-5-(4-methoxyphenyl)-1-methyl-1H-benzo[e][1,4]diazepin-2(3H)-one $^1$H NMR (300 MHz, $CDCl_3$) δ 1.21 (t, 6H), 2.58 (q, 4H), 3.40 (s, 3H), 3.52 (d, 2H), 3.69 (t, 1H), 3.84 (s, 3H), 6.85-6.95 (m, 3H; contains d at 6.90), 7.02 (fine d, 2H), 7.2-7.3 (m, 2H; overlaps with $CHCl_3$ signal), 7.47 (dd, 1H), 7.53 (d, 2H).

(Z)-3-(4-Isopropylbenzyl)-7-chloro-5-(4-methoxyphenyl)-1-methyl-1H-benzo[e][1,4]diazepin-2(3H)-one $^1$H NMR (300 MHz, $CDCl_3$) δ 1.23 (d, 6H), 2.84 (septet, 1H), 3.39 (s, 3H), 3.51 (m, 2H), 3.69 (dd, 1H), 3.85 (s, 1H), 6.89 (m, 2H), 7.12 (m, 2H), 7.26 (m, 4H), 7.44-7.54 (m, 3H).

(Z)-3-(2,5-Diisopropylbenzyl)-7-chloro-5-(4-methoxyphenyl)-1-methyl-1H-benzo[e][1,4]diazepin-2(3H)-one $^1$H NMR (300 MHz, DMSO-$d_6$) δ 0.96 (d, 3H), 1.1 (d, 3H), 1.14 (d, 3H), 1.16 (d, 3H), 2.8 (septet, 1H), 3.17 (septet, 1H), 3.35 (s, 3H), 3.40 (m, 2H), 3.70 (m, 1H), 3.80 (s, 3H), 6.9-7.2 (m, 6H), 7.45 (d, 2H), 7.6 (d, 1H), 7.7 (d, 1H).

(Z)-3-(3-Bromobenzyl)-1-(4-methoxybenzyl)-7-chloro-5-(4-methoxyphenyl)-1H-benzo[e][1,4]-diazepin-2(3H)-one To a stirred and cooled (dry ice/acetone bath) solution of E2 (6.00 g, 14.2 mmol) in THF (80 mL) was slowly added 1 M KO$^t$Bu (21 mL, 21 mmol, 1.5 eq). The resulting deep red mixture was stirred over dry ice/acetone bath ~10 min followed by the slow addition of a solution of 3-bromobenzyl bromide (5.10 g, 21.4 mmol, 1.5 eq) in THF (15 mL). After stirring another ~45 min at −78° C., the reaction mixture was quenched with saturated brine and diluted with EtOAc. The organic layer was dried ($Na_2SO_4$), filtered and evaporated (rotovap, then high vacuum). Chromatography over silica gel using 10-30% EtOAc/heptane gave 7.08 g (yield of 84%) of the title product. Noting that when using benzyl chlorides as alkylating agents, tetrabutyl ammonium iodide was added along with the alkylating agent at low temperature. $^1$H NMR (300 MHz, $CDCl_3$) δ 3.57 (d, 2H), 3.70 (s, 3H), 3.73 (t, 1H), 3.83 (s, 3H), 4.59 (d, 1H), 5.62 (d, 1H), 6.61 (d, 2H), 6.8-6.9 (m, 4H), 7.2-7.45 (m, 8H), 7.63 (fine d, 1H).

The following compounds were prepared by making the appropriate substitutions to the above procedures.

(Z)-3-(2,6-Dimethylbenzyl)-7-chloro-1-(4-methoxybenzyl)-5-(4-methoxyphenyl)-1H-benzo[e][1,4]diazepin-2(3H)-one $^1$H NMR (300 MHz, $CDCl_3$) δ 2.41 (s, 6H), 3.50 (dd, 1H), 3.70 (s, 3H), 3.79 (dd, 1H), 3.84 (s, 3H), 3.90 (dd, 1H), 4.58 (d, 1H), 5.69 (d, 1H), 6.62 (d, 2H), 6.83 (d, 2H), 6.90 (d, 2H), 6.95-7.03 (m, 3H), 7.06 (fine d, 1H), 7.16 (d, 2H), 7.32 (d, 1H), 7.37 (dd, 1H).

(Z)-3-(3,5-Dimethylbenzyl)-7-chloro-1-(4-methoxybenzyl)-5-(4-methoxyphenyl)-1H-benzo[e][1,4]diazepin-2(3H)-one $^1$H NMR (300 MHz, DMSO-d$_6$) δ 2.2 (s, 6H), 3.3 (m, 2H), 3.6 (s, 3H), 3.7 (m, 1H), 3.85 (s, 3H), 5.8 (d, 1H), 6.45 (d, 1H), 6.65 (d, 2H), 6.85 (m, 3H), 6.95 (m, 3H), 7.1 (s, 1H), 7.2 (d, 2H), 7.6 (d, 1H), 7.7 (d, 1H).

(Z)-3-(3,4-Dimethylbenzyl)-7-chloro-1-(4-methoxybenzyl)-5-(4-hydroxyphenyl)-1H-benzo[e][1,4]diazepin-2(3H)-one $^1$H NMR (300 MHz, DMSO-d$_6$) δ 2.10 (s, 6H; 2 methyl groups), 3.39 (m, 2H, contains benzylic protons and H$_2$O signal), 3.68 (s, 3H), 3.81-3.89 (m, 4H, contains N-PMB-OMe signal), 4.99 (d, 1H), 5.41 (d, 1H), 6.71 (d, 2H), 6.88 (d, 2H), 7.0-7.2 (m, 6H), 7.31 (d, 2H), 7.65 (m, 2H)

(Z)-3-(2,6-Diethylbenzyl)-7-chloro-1-(4-methoxybenzyl)-5-(4-methoxyphenyl)-1H-benzo[e][1,4]diazepin-2(3H)-one $^1$H NMR (300 MHz, CDCl$_3$) δ 1.18 (t, 6H), 2.65-2.95 (m, 4H), 3.59 (dd, 1H), 3.70 (s, 3H), 3.74 (dd, 1H), 3.83 (s, 3H), 3.90 (dd, 1H), 4.58 (d, 1H), 5.71 (d, 1H), 6.62 (d, 2H), 6.82 (d, 2H), 6.89 (d, 2H), 7.0-7.1 (m, 3H), 7.1-7.2 (m, 3H), 7.32 (d, 1H), 7.36 (dd, 1H).

(Z)-3-(3,4-Diethylbenzyl)-7-chloro-1-(4-methoxybenzyl)-5-(4-methoxyphenyl)-1H-benzo-[e][1,4]diazepin-2(3H)-one

(Z)-3-(3,5-Diethylbenzyl)-1-(4-methoxybenzyl)-7-chloro-5-(4-hydroxyphenyl)-1H-benzo[e][1,4]diazepin-2(3H)-one $^1$H NMR (300 MHz, CDCl$_3$) δ 1.21 (t, 6H), 2.59 (q, 4H), 3.5-3.65 (m, 2H), 3.70 (s, 3H), 3.76 (dd, 1H), 3.85 (s, 3H), 6.61 (d, 2H), 6.8-6.95 (m, 5H), 7.04 (fine d, 2H), 7.10 (fine d, 1H), 7.2-7.28 (m, 2H; overlaps with CHCl$_3$ signal), 7.30 (d, 1H), 7.37 (dd, 1H).

(Z)-3-(4-Isopropylbenzyl)-7-chloro-1-(4-methoxybenzyl)-5-(4-hydroxyphenyl)-1H-benzo[e][1,4]diazepin-2(3H)-one $^1$H NMR (300 MHz, DMSO-d$_6$) δ 1.15 (d, 6H), 2.85 (septet, 1H), 3.25-3.45 (m, 3H), 3.65 (s, 3H), 3.75-3.85 (m, 4H), 4.80 (d, 1H), 5.45 (d, 1H), 6.60 (m, 2H), 6.85 (m, 2H), 6.95 (m, 2H), 7.0-7.3 (m, 6H), 7.63 (dd, 1H), 7.74 (d, 1H).

(Z)-3-(2,5-Diisopropylbenzyl)-1-(4-methoxybenzyl)-7-chloro-5-(4-hydroxyphenyl)-1H-benzo[e][1,4]diazepin-2(3H)-one $^1$H NMR (300 MHz, DMSO-d$_6$) δ 1.1 (d, 3H), 1.2 (d, 3H), 1.25 (m, 6H), 2.87 (septet, 1H), 3.2 (septet, 1H), 3.6-3.7 (m, 5H), 3.8 (m, 1H), 3.9 (s, 3H), 4.55 (d, 1H), 6.7 (d, 1H), 6.58 (m, 2H), 6.8 (m, 2H), 6.9 (m, 2H), 7.0-7.4 (m, 8H).

7-Chloro-5-(4-fluorophenyl)-3-(2-methylbenzyl)-1H-benzo[e][1,4]diazepin-2(3H)-one 7-Chloro-5-(4-fluorophenyl)-1-(4-methoxybenzyl)-1H-benzo[e][1,4]diazepin-2(3H)-one (90 mg, 0.220 mmol) was dissolved in dry THF (2 mL) and cooled to −78° C. under nitrogen. Potassium tert-butoxide (49 mg, 0.437 mmol) was added as a solid in one portion and the resulting red solution was stirred vigorously for 5 min. To this solution was added 2-methylbenzyl bromide (25 µL, 0.262 mmol) by syringe. The mixture was stirred for 1 h at −78° C., then the cold bath was removed. After another 1 h (warming to room temperature), the reaction was quenched with MeOH and diluted with ethyl acetate. The organic layer was washed twice with water and once with brine, and then dried over MgSO$_4$. Chromatography on silica gel eluting with 100% hexanes to 30% ethyl acetate in hexanes provided 7-chloro-5-(4-fluorophenyl)-1-(4-methoxybenzyl)-3-(2-methylbenzyl)-1H-benzo[e][1,4]diazepin-2(3H)-one (44 mg, 39%). APCI MS m/z 535.2 [M+Na$^+$], 513.3 [M$^+$]; $^1$H NMR (300 MHz, CDCl$_3$) δ 7.43-6.98 (m, 11H), 6.88 (d, J=9 Hz, 2H), 6.61 (dd, J=7 Hz, 2 Hz, 2H), 5.69 (d, J=15 Hz, 1H), 4.55 (d, J=15 Hz, 1H), 3.85 (t, J=7 Hz, 1H), 3.70 (s, 3H), 3.63 (d, J=7 Hz, 2H), 2.37 (s, 3H).

Example 6

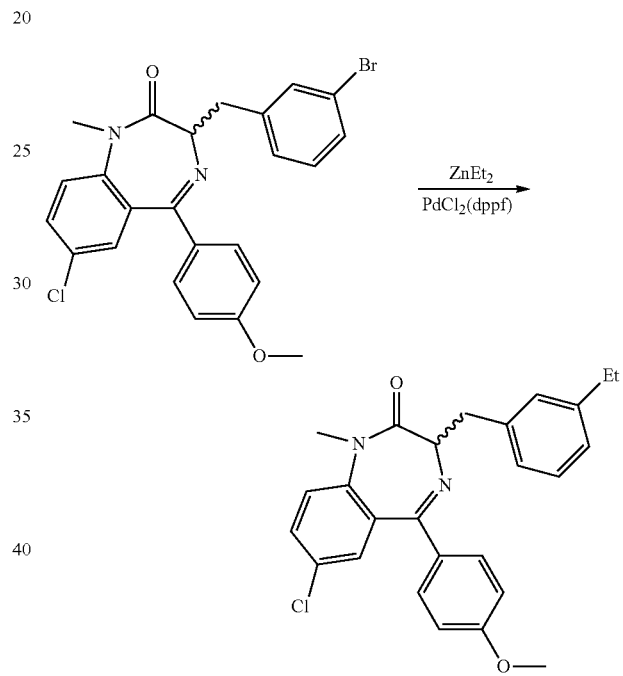

(Z)-7-Chloro-3-(3-ethylbenzyl)-5-(4-methoxyphenyl)-1-methyl-1H-benzo[e][1,4]diazepin-2(3H)-one To a stirred and cooled (dry ice-acetone bath) solution of ArBr (1.21 g, 2.5 mmol) and PdCl$_2$(dppf)[0.22 g] in dry THF (10 mL) was added 1 M Et$_2$Zn (9.3 mL, 10 mmol, 4 eq). After warming to RT, the reaction mixture was stirred at 50° C. until HPLC indicated reaction to be complete. After aqueous workup, chromatography gave 0.95 g (yield of 88%) of title product. $^1$H NMR (300 MHz, CDCl$_3$) δ 1.22 (t, 3H), 2.62 (q, 2H), 3.55 (d, 2H), 3.70 (t, 1H), 3.84 (s, 3H), 6.89 (d, 2H), 7.03 (m, 1H), 7.1-7.3 (m, 5H), 7.4-7.55 (m, 3H).

The following compounds were made by making the appropriate substitutions to the above procedure.

(Z)-7-Chloro-3-(3-ethylbenzyl)-1-(4-methoxybenzyl)-5-(4-methoxyphenyl)-1H-benzo[e][1,4]diazepin-2(3H)-one $^1$H NMR (300 MHz, CDCl$_3$) δ 1.23 (t, 3H), 2.63 (q, 2H), 3.55-3.65 (m, 2H), 3.68 (s, 3H), 3.80 (dd, 1H), 3.83 (s, 3H), 4.59 (d, 1H), 5.63 (d, 1H), 6.61 (d, 2H), 6.85 (d, 2H), 6.88 (d, 2H), 7.04 (dt, 1H), 7.10 (fine d, 1H), 7.13-7.26 (m, 5H), 7.30 (d, 1H), 7.37 (dd, 1H).

(Z)-7-Chloro-3-(3-isopropylbenzyl)-5-(4-methoxyphenyl)-1-methyl-1H-benzo[e][1,4]diazepin-2(3H)-one $^1$H NMR (300 MHz, CDCl$_3$) δ 1.24/1.25 (2 overlapping doublets, 6H), 2.88 (heptet, 1H), 3.38 (s, 3H), 3.5-3.6 (m, 2H), 3.69 (t, 1H), 3.84 (s, 3H), 6.89 (d, 2H), 7.07 (dt, 1H), 7.13 (dt, 1H), 7.15-7.3 (m, 4H; includes CHCl$_3$ singlet), 7.47 (dd, 1H), 7.52 (d, 2H).

Example 7

Representative Procedures for Removal of a p-Methoxybenzyl Group

Method A

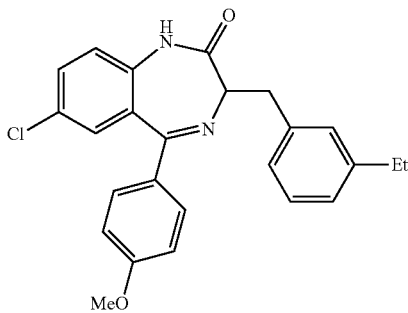 [SMILES: CCc1cccc(CC2N=C(c3ccc(OC)cc3)c3cc(Cl)ccc3NC2=O)c1]

(Z)-3-(3-Ethylbenzyl)-7-chloro-5-(4-methoxyphenyl)-1H-benzo[e][1,4]diazepin-2(3H)-one To a solution of N1-PMB-protected benzodiazepinone (1 g) in MeCN (17 mL) and H$_2$O (3 mL) was added cerium (IV) ammonium nitrate (7 g). The resulting mixture was stirred until TLC showed reaction to be complete and was then diluted with water, EtOAc and heptane. The organic layer was dried (Na$_2$SO$_4$), filtered and evaporated to a crude solid. Chromatography using increasing amounts of DCM/EtOAc (1:1) in heptane (up to 25:25:50 DCM/EtOAc/heptane) gave 0.55 g (yield of 57%) of title product. $^1$H NMR (300 MHz, DMSO-d$_6$) δ 1.19 (t, 3H), 2.57 (q, 2H), 3.2-3.4 (m, 2H), 3.7-3.8 (m, 4H; contains OMe singlet at 3.79), 7.0-7.1 (m, 3H), 7.1-7.35 (m, 5H), 7.39 (d, 2H), 7.71 (dd, 1H), 10.9 (br s, 1H).

The following compounds were made by making the appropriate substitutions to the above procedure.

(Z)-3-(2,5-Dimethylbenzyl)-7-chloro-5-(4-methoxyphenyl)-1H-benzo[e][1,4]diazepin-2(3H)-one $^1$H NMR (300 MHz, DMSO-d$_6$) δ 2.21 (s, 3H), 2.28 (s, 3H), 3.23-3.37 (m, 2H), 3.63 (m, 1H), 3.85 (s, 3H), 6.86-7.4 (m, 9H), 7.55 (dd, 1H), 10.65 (s, 1H).

Z)-3-(3,5-Dimethylbenzyl)-7-chloro-5-(4-methoxyphenyl)-1H-benzo[e][1,4]diazepin-2(3H)-one $^1$H NMR (300 MHz, DMSO-d$_6$) δ 2.25 (s, 6H), 3.25 (m, 2H), 3.85 (m., 4H), 6.8-7.8 (m, 10H), 10.9 (s, 1H).

(Z)-3-(4-Isopropylbenzyl)-7-chloro-5-(4-methoxyphenyl)-1H-benzo[e][1,4]diazepin-2(3H)-one $^1$H NMR (300 MHz, DMSO-d$_6$) δ 1.15 (d, 6H), 2.85 (septet, 1H), 3.25-3.38 (m, 2H), 3.8 (br s, 4H), 6.95-7.50 (m, 10H), 7.73 (dd, 1H), 10.9 (s, 1H).

Method B (Z)-3-(2,6-Dimethylbenzyl)-7-chloro-5-(4-methoxyphenyl)-1H-benzo[e][1,4]diazepin-2(3H)-one A mixture of PMB-protected benzodiazepinone (0.78 g, 1.45 mmol), anisole (25 mL), and AlBr$_3$ (3.8 g) was stirred at 85° C. (1 h), allowed to cool, then treated with ice and diluted with EtOAc and heptane. The organic layer was removed, dried (Na$_2$SO$_4$), filtered, concentrated to a volume of ~2 mL, and chromatographed (step-wise gradient up to 50% EtOAc/heptane) to give the title product in 89% yield. $^1$H NMR (300 MHz, CDCl$_3$) δ 2.42 (s, 6H), 3.43 (dd, 1H), 3.65-3.9 (m, 5H; contains OMe singlet at 3.82), 6.88 (d, 2H), 7.0-7.1 (m, 4H), 7.2-7.3 (m, 1H; overlaps with CHCl$_3$ signal), 7.32 (d, 2H), 7.43 (dd, 1H), 7.9 (s, 1H).

The following compounds were made by making the appropriate substitutions to the above procedure.

(Z)-3-(2,6-Diethylbenzyl)-7-chloro-5-(4-methoxyphenyl)-1H-benzo[e][1,4]diazepin-2(3H)-one $^1$H NMR (300 MHz, CDCl$_3$) δ 1.20 (t, 6H), 2.7-3.0 (m, 4H), 3.51 (dd, 1H), 3.68 (dd, 1H), 3.75-3.9 (m, 4H; contains OMe singlet at 3.83), 6.86 (d, 2H), 7.0-7.2 (m, 4H), 7.2-7.3 (m, 1H; overlaps with CHCl$_3$ signal), 7.32 (d, 2H), 7.43 (dd, 1H), 7.96 (br s, 1H).

(Z)-3-(3,4-Diethylbenzyl)-7-chloro-5-(4-methoxyphenyl)-1H-benzo[e][1,4]diazepin-2(3H)-one $^1$H NMR (300 MHz, DMSO-d$_6$) δ 1.12 (m, 6H), 2.45-2.75 (m, 4H; contains DMSO signal), 3.2-3.35 (m, 2H; contains benzylic protons and H$_2$O signals), 3.65 (m, 1H), 3.80 (s, 3H), 6.99 (d, 2H), 7.09 (m, 1H), 7.15 (s, 1H), 7.21-7.27 (m, 2H), 7.38 (d, 2H), 7.62 (fine dd, 1H), 10.71 (s, 1H).

(Z)-3-(3,5-Diethylbenzyl)-7-chloro-5-(4-methoxyphenyl)-1H-benzo[e][1,4]diazepin-2(3H)-one $^1$H NMR (300 MHz, CDCl$_3$) δ 1.23 (t, 6H), 2.60 (q, 4H), 3.51 (d, 2H), 3.72 (t, 1H), 3.83 (s, 3H), 6.85-6.95 (m, 3H), 7.0-7.1 (m, 3H), 7.29 (fine d, 1H), 7.4-7.5 (m, 3H), 8.32 (br s, 1H).

(Z)-3-(2,5-Diisopropylbenzyl)-7-chloro-5-(4-methoxyphenyl)-1H-benzo[e][1,4]diazepin-2(3H)-one MS, m/z=475.2 [M+1].

Method C

7-Chloro-5-(4-fluorophenyl)-3-(2-methylbenzyl)-1H-benzo[e][1,4]diazepin-2(3H)-one 7-Chloro-5-(4-fluorophenyl)-1-(4-methoxybenzyl)-3-(2-methylbenzyl)-1H-benzo[e][1,4]diazepin-2(3H)-one (44 mg, 0.086 mmol) was dissolved in dichloroethane (1 mL) under nitrogen and 200 μL of anisole was added followed by AlCl$_3$ (69 mg, 0.515 mmol). This mixture was heated to 85° C. for 2.5 h then allowed to cool and diluted with ethyl acetate and ice. This biphasic mixture was stirred vigorously for 20 min, then partitioned, and the organic layer was washed with water twice, then brine once. The aqueous layers were back-extracted once with ethyl acetate, and the combined organic extracts dried over MgSO$_4$. Chromatography on silica gel (5%-30%-40%-50% ethyl acetate in hexanes) provided the title compound (27 mg, 80%) as a yellow solid. APCI MS m/z 415.1 [M+Na$^+$], 393.1 [M+H$^+$]; $^1$H NMR (300 MHz, CDCl$_3$) δ 9.28 (s, 1H), 7.61-7.16 (m, 11H), 3.91 (t, J=7 Hz, 1H), 3.72-3.69 (m, 2H), 2.50 (s, 3H).

Example 8

Representative Procedure for O-Demethylation of a p-Methoxybenzyl Group (Z)-7-Chloro-5-(4-hydroxyphenyl)-3-(2-methylbenzyl)-1H-benzo[e][1,4]diazepin-2(3H)-one To a solution of ArOMe precursor (0.6 g, 1.4 mmol) in CH$_2$Br$_2$ (20 mL) was added EtSH (7 mL) and then AlBr$_3$ (1.7 g, 6.3 mmol, 4.5 eq). The resulting mixture was stirred overnight and then treated with ice (20 g) and after one hour filtered. The resulting solid was triturated with 50% DCM/heptane and then vacuum dried to give 445 mg (yield of 80%) of the title product as a light yellow solid. $^1$H NMR (300 MHz, DMSO-d$_6$) δ 2.31 (s, 3H), 3.25-3.45 (m, 2H), 3.73 (dd, 1H), 6.80 (d, 2H), 7.02-7.18 (m, 3H), 7.2-7.3 (m, 5H), 7.64 (dd, 1H), 10.0 (br s, 1H), 10.7 (br s, 1H). MS, m/z 391.7 [M+1]

The following compounds were made by making the appropriate substitutions to the above procedure.

(Z)-7-Chloro-5-(4-hydroxyphenyl)-3-(2-methylbenzyl)-1-methyl-1H-benzo[e][1,4]diazepin-2(3H)-one $^1$H NMR (300 MHz, DMSO-d$_6$) δ 2.32 (s, 3H), 3.3-3.5 (m, 5H; contains singlet for NMe at 3.36), 3.90 (t, 1H), 6.87 (d, 2H), 7.05-7.15 (m, 3H), 7.20 (m, 1H), 7.29 (fine d, 1H), 7.35 (d, 2H), 7.65 (d, 1H), 7.78 (dd, 1H), 9-11 (br s, 1H). MS, m/z 405.3 [M+1].

(Z)-3-(2,3-Dimethylbenzyl)-7-chloro-5-(4-hydroxyphenyl)-1H-benzo[e][1,4]diazepin-2(3H)-one $^1$H NMR (300 MHz, DMSO-d$_6$) δ 2.18 (d, 6H; 2 methyl groups), 3.35-3.5 (m, 2H; contains H$_2$O signal), 3.65 (t, 1H), 6.78 (d, 2H), 6.98 (d, 2H), 7.09 (t, 1H), 7.22-7.27 (m, 4H), 7.62 (dd, 1H), 9.92 (br s, 1H), 10.7 (s, 1H). MS, m/z 405.2 [M+1]

(Z)-3-(2,6-Dimethylbenzyl)-7-chloro-5-(4-hydroxyphenyl)-1H-benzo[e][1,4]diazepin-2(3H)-one $^1$H NMR (300 MHz, DMSO-d$_6$) δ 2.32 (s, 6H), 3.21 (dd, 1H), 3.55-3.7 (m, 2H), 6.77 (d, 2H), 6.98 (s, 3H), 7.13 (d, 2H), 7.18 (fine d, 1H), 7.26 (d, 1H), 7.60 (dd, 1H), 9.92 (br s, 1H), 10.7 (s, 1H); MS, m/z 405.2 [M+1].

(Z)-3-(2,6-Dimethylbenzyl)-7-chloro-5-(4-hydroxyphenyl)-1-methyl-1H-benzo[e][1,4]diazepin-2(3H)-one $^1$H NMR (300 MHz, DMSO-d$_6$) δ 2.31 (s, 6H), 3.20 (dd, 1H), 3.33 (s, 3H), 3.6-3.7 (m, 2H), 6.78 (d, 2H), 6.96 (s, 3H), 7.18 (fine d, 1H), 7.22 (d, 2H), 7.60 (d, 1H), 7.68 (dd, 1H), 9.97 (s, 1H); MS, m/z 419.2 [M+1].

(Z)-3-(3,5-Dimethylbenzyl)-7-chloro-5-(4-hydroxyphenyl)-1H-benzo[e][1,4]diazepin-2(3H)-one $^1$H NMR (300 MHz, DMSO-d$_6$) δ 2.33 (s, 6H), 3.1-3.35 (m, 3H), 3.55 (m, 1H), 6.65 (m, 3H), 6.90 (d, 2H), 7.30-7.40 (m, 4H), 7.60 (dd, 1H), 9.95 (s, 1H), 10.63 (s, 1H); MS, m/z 405.2 [M+1].

(Z)-3-(3,5-Dimethylbenzyl)-7-chloro-5-(4-hydroxyphenyl)-1-methyl-1H-benzo[e][1,4]diazepin-2(3H)-one $^1$H NMR (300 MHz, DMSO-d$_6$), δ 2.20 (s, 6H), 3.24-3.31 (m, 5H), 3.61 (m, 1H), 6.78-6.90 (m, 5H), 7.22 (d, 1H), 7.35 (m, 2H), 7.57 (d, 1H), 7.67 (dd, 1H), 9.98 (s, 1H); MS, m/z 419.3 [M+1].

(Z)-3-(3,4-Dimethylbenzyl)-7-chloro-5-(4-hydroxyphenyl)-1H-benzo[e][1,4]diazepin-2(3H)-one $^1$H NMR (300 MHz, DMSO-d$_6$) δ 2.18 (fine d, 6H), 3.15-3.45 (m, 2H; contains water signal), 3.59 (t, 1H), 6.80 (d, 2H), 7.01 (s, 2H), 7.08 (s, 1H), 7.22 (m, 2H), 7.28 (d, 2H), 7.59 (fine dd, 1H), 9.98 (br s, 1H), 10.65 (s, 1H); MS, m/z 405.8 [M+1].

(Z)-3-(2,6-Diethylbenzyl)-7-chloro-5-(4-hydroxyphenyl)-1H-benzo[e][1,4]diazepin-2(3H)-one $^1$H NMR (300 MHz, DMSO-d$_6$) δ 1.09 (t, 6H), 2.6-2.9 (m, 4H), 3.27 (m, overlaps with H$_2$O signal), 3.51 (dd, 1H), 3.61 (dd, 1H), 6.77 (d, 2H), 6.96-7.2 (m, 6H), 7.26 (d, 1H), 7.60 (d, 1H), 9.93 (br s, 1H), 10.7 (s, 1H); MS, m/z 433.2 [M+1].

(Z)-3-(2,6-Diethylbenzyl)-7-chloro-5-(4-hydroxyphenyl)-1-methyl-1H-benzo[e][1,4]diazepin-2(3H)-one $^1$H NMR (300 MHz, DMSO-d$_6$) δ 1.07 (t, 6H), 2.6-2.85 (m, 4H), 3.2-3.4 (m, contains signals for C-3 methine proton, NMe, and H$_2$O), 3.5-3.7 (m, 2H), 6.78 (d, 2H), 6.94-7.02 (m, 2H), 7.08 (dd, 1H), 7.18 (fine d, 1H), 7.23 (d, 2H), 7.60 (d, 1H), 7.69 (dd, 1H), 9.97 (s, 1H); MS, m/z 447.3 [M+1].

(Z)-3-(3,4-Diethylbenzyl)-7-chloro-5-(4-hydroxyphenyl)-1H-benzo[e][1,4]diazepin-2(3H)-one $^1$H NMR (300 MHz, DMSO-d$_6$) δ 1.07 (m, 6H), 2.48-2.69 (m, 4H, contains DMSO signal), 3.20-3.45 (m, contains signals for benzylic protons and H$_2$O), 3.64 (fine dd, 1H), 6.82 (d, 2H), 7.03 (m, 2H), 7.12 (s, 1H), 7.2-7.25 (m, 2H), 7.29 (d, 2H), 7.60 (fine dd, 1H), 9.97 (s, 1H), 10.68 (s, 1H); MS, m/z 433.3 [M+1].

(Z)-3-(3,4-Diethylbenzyl)-7-chloro-5-(4-hydroxyphenyl)-1-methyl-1H-benzo[e][1,4]diazepin-2(3H)-one $^1$H NMR (300 MHz, DMSO-d$_6$) δ 1.07 (m, 6H), 2.48-2.59 (m, 4H, contains DMSO signal), 3.25-3.33 (m, contains signals for benzylic protons, NMe, and H$_2$O), 3.64 (fine dd, 1H), 6.82 (d, 2H), 7.01 (s, 2H), 7.09 (s, 1H), 7.23 (fine d, 1H), 7.38 (d, 2H), 7.59 (d, 1H), 7.68 (fine dd, 1H), 9.97 (s, 1H); MS, m/z 447.2 [M+1].

(Z)-3-(3,5-Diethylbenzyl)-7-chloro-5-(4-hydroxyphenyl)-1H-benzo[e][1,4]diazepin-2(3H)-one $^1$H NMR (300 MHz, DMSO-d$_6$) δ 1.18 (t, 6H), 2.55 (q, 4H), 3.25-3.4 (m, 2H), 3.88 (br t, 1H), 6.85-6.92 (m, 3H), 7.03

(s, 1H), 7.27-7.35 (m, 4H), 7.75 (dd, 1H), 10-11 (br s), 11.03 (br s, 1H); MS, m/z 433.3 [M+1].

(Z)-3-(3,5-Diethylbenzyl)-7-chloro-5-(4-hydroxyphenyl)-1-methyl-1H-benzo[e][1,4]diazepin-2(3H)-one $^1$H NMR (300 MHz, DMSO-$d_6$) δ 1.14 (t, 6H), 2.52 (q, overlaps with DMSO multiplet), 3.30 (t, 2H), 3.68 (t, overlaps with H$_2$O signal), 6.78-6.86 (m, 3H), 6.96 (fine d, 1H), 7.22 (fine d, 1H), 7.37 (d, 2H), 7.59 (d, 1H), 7.69 (dd, 1H), 10.00 (br s, 1H); MS, m/z 447.3 [M+1].

(Z)-3-(4-Isopropylbenzyl)-7-chloro-5-(4-hydroxyphenyl)-1H-benzo[e][1,4]diazepin-2(3H)-one $^1$H NMR (300 MHz, DMSO-$d_6$) 1.15 (d, 6H), 2.82 (septet, 1H), 3.24-3.38 (m, 2H), 3.63 (m, 1H), 6.79 (m, 2H), 7.10-7.30 (m, 8H), 7.59 (dd, 1H), 9.45 (s, 1H), 10.61 (s, 1H); MS, m/z 419.3 [M+1].

(Z)-3-(4-Isopropylbenzyl)-7-chloro-5-(4-hydroxyphenyl)-1-methyl-1H-benzo[e][1,4]diazepin-2(3H)-one $^1$H NMR (300 MHz, DMSO-$d_6$) δ 1.15 (d, 6H), 2.84 (septet, 1H), 3.26-3.41 (m, 5H), 3.77 (m, 1H), 6.84 (m, 2H), 7.10-7.40 (m, 7H), 7.63 (d, 1H), 7.73 (dd, 1H), 10.2 (br s, 1H); MS, m/z 433.3 [M+1].

(Z)-3-(2,5-Diisopropylbenzyl)-7-chloro-5-(4-hydroxyphenyl)-1H-benzo[e][1,4]diazepin-2(3H)-one $^1$H NMR (300 MHz, DMSO-$d_6$) δ 1.02 (d, 3H), 1.12 (d, 3H), 1.17 (d, 3H), 1.19 (d, 3H), 2.81 (septet, 1H), 3.18 (septet, 1H), 3.37 (d, 2H), 3.58 (t, 1H), 6.74 (d, 2H), 7.04 (dd, 1H), 7.12-7.26 (m, 6H), 7.60 (dd, 1H), 9.94 (s, 1H), 10.68 (s, 1H); MS, m/z 461.4 [M+1].

(Z)-3-(2,5-Diisopropylbenzyl)-7-chloro-5-(4-hydroxyphenyl)-1-methyl-1H-benzo[e][1,4]diazepin-2(3H)-one $^1$H NMR (300 MHz, DMSO-$d_6$) δ 0.98 (d, 3H), 1.12 (d, 3H), 1.15 (d, 3H), 1.18 (d, 3H), 2.80 (septet, 1H), 3.15 (septet, 1H), 3.39 (m, 2H), 3.64 (m, 1H), 6.76 (d, 2H), 7.03 (dd, 1H), 7.15 (m, 2H), 7.20 (d, 1H), 7.32 (d, 2H), 7.58-7.7 (m, 2H), 9.97 (s, 1H); MS, m/z 475.2 [M+1].

Example 9

Representative Palladium Coupling Procedure for Making a C5-fluorophenyl-benzo[e][1,4]diazepin-2(3H)-one (Z)-7-Chloro-3-(3,4-diethylbenzyl)-5-(4-fluorophenyl)-1-methyl-1H-benzo[e][1,4]diazepin-2(3H)-one A 10 mL sealed tube was charged with (E)-5,7-dichloro-3-(3,4-diethylbenzyl)-1-methyl-1H-benzo[e][1,4]diazepin-2(3H)-one (0.25 g, 0.505 mmol, 1 equivalent), 4-fluorophenylboronic acid (0.071 g, 0.505 mmol, 1 equivalent), Pd(OAc)$_2$ (0.2 equivalents), PPh$_3$ (0.2 equivalents), Cs$_2$CO$_3$ (2 equivalents) and DMF (3 mL). The tube was evacuated, flushed with nitrogen gas and placed in an oil bath at 100° C. for 1.5 hour. The mixture was cooled to ambient temperature, diluted with ethyl acetate (10 mL) and water (5 mL), and filtered through a pad of celite. The layers were separated and the organic phase was washed with brine (3×10 mL), dried over sodium sulfate, filtered, and concentrated. The residue was purified by chromatography (silica gel, 70:30 hexanes:ethyl acetate) to provide an oil. This oil was dissolved in a mixture of acetonitrile (3 mL) and water (1 mL), and the solution was freeze-dried overnight to give (Z)-7-chloro-3-(3,4-diethylbenzyl)-5-(4-fluorophenyl)-1-methyl-1H-benzo[e][1,4]diazepin-2(3H)-one (0.12 g, 43%) as an off-white solid: mp 54-56° C.; $^1$H NMR (300 MHz, DMSO-$d_6$) δ 7.41-7.22 (m, 4H), 7.18-6.98 (m, 6H), 6.87 (d, J=8.6 Hz, 2H), 6.60 (d, J=4.6 Hz, 2H), 5.66 (d, J=15 Hz, 1H), 4.56 (d, J=15 Hz, 1H), 3.82-3.77 (m, 1H), 3.70 (s, 3H), 3.63-3.55 (m, 2H), 2.67-2.58 (m, 4H), 1.26-1.12 (m, 6H); APCI MS m/z 556 [M+H$^+$].

Example 10

Representative Procedure for Demethylation Using Aluminum Chloride (Z)-7-Chloro-3-(3,4-diethylbenzyl)-5-(4-fluorophenyl)-1H-benzo[e][1,4]diazepin-2(3H)-one To a stirred solution of (Z)-7-chloro-3-(3,4-diethylbenzyl)-5-(4-fluorophenyl)-1-methyl-1H-benzo[e][1,4]diazepin-2(3H)-one (0.1 g, 0.18 mmol) in anisole (3 mL) was added aluminum chloride (0.144 g, 1.08 mmol). The mixture was heated at 85° C. for 1 hour, cooled to ambient temperature and poured into a mixture of ice/water (10 mL) and ethyl acetate (20 mL) and stirred vigorously for 10 min. The layers were separated and the organic phase was dried over sodium sulfate, filtered, and then concentrated. The residue was purified by chromatography (silica gel, 95:5 CH$_2$Cl$_2$:MeOH) to provide an oil which was dissolved in a mixture of acetonitrile (3 mL) and water (1 mL). This solution was freeze-dried overnight to give (Z)-7-chloro-3-(3,4-diethylbenzyl)-5-(4-fluorophenyl)-1H-benzo[e][1,4]diazepin-2(3H)-one as an off-white solid: mp 88-90° C.; $^1$H NMR (300 MHz, DMSO-$d_6$) δ 10.71 (s, 1H), 7.64 (dd, J=8.8, 2.5 Hz, 1H), 7.49 (t, J=5.6 Hz, 2H), 7.30-7.23 (m, 4H), 7.13-7.01 (m, 3H), 3.65 (t, J=5.5 Hz, 1H), 3.32-3.31 (m, 2H), 2.56 (quintet, J=7.3 Hz, 4H), 1.13 (q, J=7.2 Hz, 6H); APCI MS m/z 435 [M+H$^+$].

Example 11

The compound having chemical name (Z)-7-chloro-3-(2,6-dimethylbenzyl)-5-(4-hydroxyphenyl)-1-methyl-1H-benzo[e][1,4]diazepin-2(3H)-one (i.e., "compound H") was evaluated for toxicity and inhibition of epidermal hyperplasia induced by 14 all-trans retinoic acid (RA).
General Procedures:
Human Skin.
Replicate 6-mm punch biopsies of full-thickness psoriatic plaque skin were obtained from human skin donors with psoriasis. These biopsies were used in the transplant studies. Six-mm punch biopsies of sun-protected (hip) skin from non-psoriatic donors were obtained as controls. In addition, replicate 2-mm full-thickness punch biopsies of sun-protected hip skin were obtained from normal donors for use in organ culture studies.
Human Skin Organ Cultures.
Immediately upon biopsy, the replicate 2-mm punch biopsies (non-psoriatic skin only) were immersed in culture medium consisting of Keratinocyte Basal Medium (KBM) (Lonza, Walkersville, Md.). KBM is a low-Ca$^{2+}$, serum-free modification of MCDB-153 medium. It was supplemented with CaCl$_2$ to bring the final Ca$^{2+}$ concentration to 1.4 mM.

Biopsies were incubated in wells of a 24-well dish containing 400 µl of $Ca^{2+}$-supplemented KBM with or without additional treatments (RA and/or Compound H). Cultures were incubated at 37° C. in an atmosphere of 95% air and 5% $CO_2$. Other than to maintain the tissue in a minimal volume of medium, nothing further was done to ensure a strict air-liquid interface. Incubation was for 8 days, with change of medium and fresh treatments provided every second day. At the end of the incubation period, tissue was fixed in 10% buffered formalin and examined histologically after staining with hematoxylin and eosin. Routinely, 3-6 tissue sections were prepared from each block. Epidermal thickness measurements were made at several sites in each tissue section (distance from the dermal-epidermal juncture to the top of the viable portion of the epithelium). The organ culture procedure employed here has been described in the past (Varani et al. (1993) Amer. J. Pathol. 142:189-198; and Varani et al., (1994) J. Clin. Invest. 94:1747-1753). In order to evaluate the toxicity of compound H, tissue was examined histologically and necrosis was assessed on a 0 to 4+ scale, with 0 indicating no change from control and 4+ indicating complete necrosis of the epidermis (n=6). Scores $\leq 1$ were taken as normal.

Results:

Compound H had no detectable toxicity at a dose of 0.5 µM or 1.0 µM. Slight toxicity was observed at a 2.0 µM dose of compound H. Inhibition of RA-induced epidermal hyperplasia was measured as a percent reduction in epidermal thickness (n=3). The average epidermal thickness in the absence of RA was 70-90 µm, while the average epidermal thickness was 275 µm in cells exposed to RA. As shown in Table 3, compound H caused a reduction in Retinoid-Induced Hyperplasia, as measured by a decreased in the epidermal thickness compared to cells exposed to RA alone.

TABLE 3

Inhibition of RA-Induced Epidermal Hyperplasia with Compound H.

| Dosage of Compound H (µM) | Toxicity | Percent Reduction in Retinoid-Induced Hyperplasia (%). |
|---|---|---|
| 0.5 | None detected | 40 + 10 |
| 1.0 | None detected | 48 + 15 |
| 2.0 | 2.0 + 0.5 | >95 |

Example 12

General Procedures

Human Epidermal Keratinocytes and Dermal Fibroblasts in Monolayer Culture.

Epidermal keratinocytes were isolated from fresh tissue biopsies as described previously (Varani et al., (1994) J. Clin. Invest. 94:1747-1753). Primary and early passage cells were maintained in Keratinocyte Growth Medium (KGM) (Lonza). KGM contains the same basal medium as KBM but is further supplemented with a mixture of growth factors including 0.1 ng per mL EGF, 0.5 µg per mL insulin, and 0.4% bovine pituitary extract. In addition to using low-passage keratinocytes, we also used the HaCat line of immortalized human epidermal keratinocytes in some experiments. The immortalized keratinocytes were handled exactly as low-passage keratinocytes.

Fibroblasts obtained from the same tissue were grown in monolayer culture using Dulbecco's modified minimal essential medium supplemented with nonessential amino acids and 10% fetal bovine serum (DMEM-FBS) as culture medium. Both keratinocytes and fibroblasts were maintained at 37° C. in an atmosphere of 95% air and 5% $CO_2$. Cells were subcultured by exposure to trypsin/ethylenediamine tetraacetic acid (EDTA) and used at passage 2-4. Proliferation assays. Keratinocyte proliferation was assessed by seeding $4 \times 10^4$ cells per well in a 24-well plate using KGM as culture medium. After the cells had attached (overnight), they were washed and triplicate samples were harvested for zero-time counts. The remaining cells were then incubated in KGM with different concentrations of test reagents as indicated in the Table 3. DMSO served as a negative control. Proliferation was measured on day 2 by releasing the cells with trypsin/EDTA and enumerating them using a particle counter (Coulter Electronics, Hialeah, Fla.). Fibroblast proliferation studies were conducted in a similar manner except that KBM supplemented with 1.4 mM $Ca^{2+}$ was used as culture medium.

Results:

The results of the cell proliferation assays are depicted in Table 4. KC refers to human keratinocytes. HFF refers to human foreskin fibroblasts. The cLogP values were calculated using ChemDraw™ (CambridgeSoft).

TABLE 4

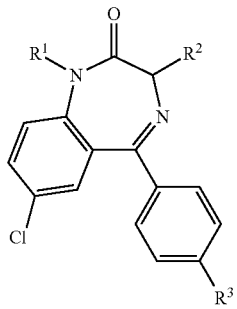

| | | | | | Percent Inhibition of Cells Per Concentration of Test Compound (µM) | | | | | |
|---|---|---|---|---|---|---|---|---|---|---|
| Compound | $R^1$ | $R^2$ | $R^3$ | cLogP | Cell | 10 | 5 | 1 | 0.5 | 0.1 | 0.05 |
| 1 | $CH_3$ | 2,6-dimethylbenzyl | OH | 5.57 | KC | $\geq$90 | $\geq$90 | $\geq$20 | <20 | <20 | <20 |
| | | | | | HFF | $\geq$90 | $\geq$90 | <20 | <20 | <20 | <20 |

TABLE 4-continued

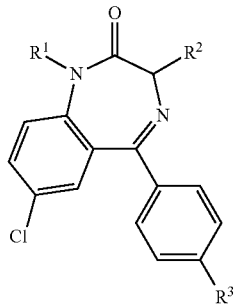

| | | | | | | Percent Inhibition of Cells Per Concentration of Test Compound (μM) | | | | | |
|---|---|---|---|---|---|---|---|---|---|---|---|
| Compound | $R^1$ | $R^2$ | $R^3$ | cLogP | Cell | 10 | 5 | 1 | 0.5 | 0.1 | 0.05 |
| 2 | $CH_3$ | 3,5-dimethylbenzyl | OH | 6.38 | KC | ≥90 | ≥90 | ≥20 | ≥20 | <20 | <20 |
| | | | | | HFF | ≥90 | ≥90 | <20 | <20 | <20 | <20 |
| 3 | H | 2,6-diethylbenzyl | OH | 6.58 | KC | ≥90 | ≥90 | ≥20 | <20 | <20 | <20 |
| | | | | | HFF | ≥90 | ≥90 | <20 | <20 | <20 | <20 |
| 4 | $CH_3$ | 3,4-diethylbenzyl | OH | 6.48 | KC | ≥90 | ≥90 | ≥20 | <20 | <20 | <20 |
| | | | | | HFF | ≥90 | ≥90 | <20 | <20 | <20 | <20 |
| 5 | H | 3,5-diethylbenzyl | OH | 6.63 | KC | ≥90 | ≥90 | ≥20 | ≥20 | <20 | <20 |
| | | | | | HFF | ≥90 | ≥90 | <20 | <20 | <20 | <20 |
| 6 | $CH_3$ | 3,5-diethylbenzyl | OH | 5.85 | KC | ≥90 | ≥90 | ≥20 | <20 | <20 | <20 |
| | | | | | HFF | ≥90 | ≥90 | <20 | <20 | <20 | <20 |
| 7 | H | 4-isopropylbenzyl | OH | 6 | KC | ≥90 | ≥90 | ≥20 | <20 | <20 | <20 |
| | | | | | HFF | ≥90 | ≥90 | <20 | <20 | <20 | <20 |
| 8 | $CH_3$ | 4-isopropylbenzyl | OH | 7.23 | KC | ≥90 | ≥90 | ≥20 | <20 | <20 | <20 |
| | | | | | HFF | ≥90 | ≥90 | <20 | <20 | <20 | <20 |
| 9 | H | 2,5-diisopropylbenzyl | OH | 7.37 | KC | ≥90 | ≥90 | ≥20 | ≥20 | <20 | <20 |
| | | | | | HFF | ≥90 | ≥90 | <20 | <20 | <20 | <20 |
| 10 | $CH_3$ | 2,5-diisopropylbenzyl | OH | 5.46 | KC | ≥90 | ≥90 | ≥20 | <20 | <20 | <20 |
| | | | | | HFF | ≥90 | ≥90 | <20 | <20 | <20 | <20 |
| 11 | H | 3,4-diethylbenzyl | F | 7.11 | KC | ≥90 | ≥90 | <20 | <20 | <20 | <20 |
| | | | | | HFF | ≥90 | <20 | <20 | <20 | <20 | <20 |

Based on the data from the cell proliferation assays, compound H has an $EC_{50}$ of 0.7±0.1 μM against proliferation of human keratinocyte cells and an $EC_{50}$ of 1.4±0.3 μM against proliferation of human foreskin fibroblasts.

Example 13

The compounds described herein can be tested for activity against $F_1F_0$-ATPase by measuring ATP synthesis and ATP hydrolysis. In addition, the compounds described herein can be evaluated for cytotoxicity against Ramos cells Inhibition of ATP synthesis and hydrolysis by the $F_1F_0$-ATPase and cytotoxicity in Ramos cells can be measured as described in K. M. Johnson et al. in *Chemistry & Biology* (2005) Vol. 12, pp. 485-496. Testing of 7-Chloro-5-(4-fluorophenyl)-3-(2-methylbenzyl)-1H-benzo[e][1,4]diazepin-2(3H)-one using these procedures indicated that this compound has an $IC_{50}$ of 9.1 μM in inhibiting ATP synthesis by ATPase, and has an $EC_{50}$ of 7.9 μM in causing death of Ramos cells.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

I claim:

1. A compound represented by formula I:

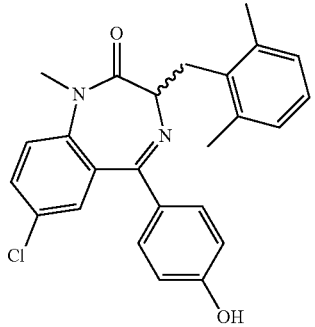

or a pharmaceutically acceptable salt thereof, wherein the stereochemical configuration at a stereocenter in a compound represented by formula I is R, S, or a mixture thereof.

2. The compound of claim 1, wherein the compound is

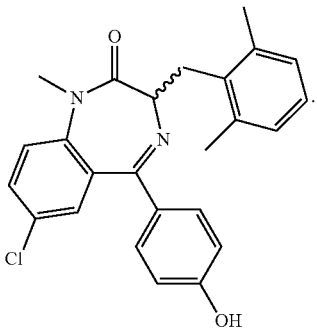 [SMILES: Cc1cccc(C)c1CC1N=C(c2ccc(O)cc2)c2cc(Cl)ccc2N(C)C1=O]

3. The compound of claim 1, wherein the stereochemical configuration at the stereocenter in the compound is (R).

4. The compound of claim 1, wherein the stereochemical configuration at the stereocenter in the compound is (S).

5. A compound represented by formula I:

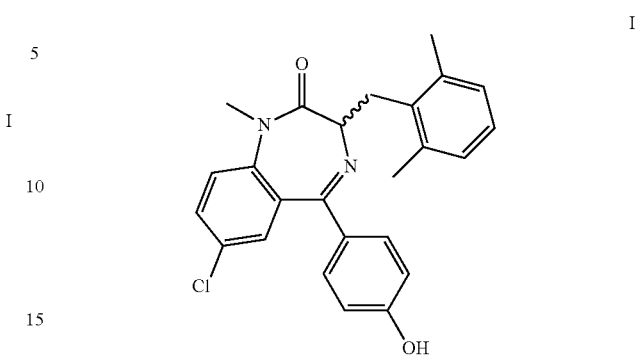

wherein the stereochemical configuration at the stereocenter in the compound of formula I is (R).

6. A pharmaceutical composition comprising a compound of claim 1 and a pharmaceutically acceptable carrier.

7. The pharmaceutical composition of claim 6, wherein the stereochemical configuration at the stereocenter in the compound of claim 1 is (R).

8. The pharmaceutical composition of claim 6, wherein the stereochemical configuration at the stereocenter in the compound of claim 1 is (S).

9. A pharmaceutical composition comprising a compound of claim 5 and a pharmaceutically acceptable carrier.

10. A method of treating a skin condition selected from the group consisting of atopic dermatitis, rosacea, psoriasis, and a skin condition associated with epidermal hyperplasia, comprising administering a therapeutically effective amount of a compound of claim 1 to a subject in need thereof to ameliorate a symptom of the skin condition.

11. The method of claim 10, wherein the skin condition is associated with epidermal hyperplasia.

12. The method of claim 10, wherein the skin condition is atopic dermatitis, rosacea, or psoriasis.

13. The method of claim 10, wherein the skin condition is psoriasis.

14. The method of claim 10, wherein the stereochemical configuration at the stereocenter in the compound of claim 1 is (R).

15. The method of claim 10, wherein the stereochemical configuration at the stereocenter in the compound of claim 1 is (S).

16. A method of treating epidermal hyperplasia, comprising administering a therapeutically effective amount of a compound of claim 1 to a subject in need thereof to ameliorate a symptom of the epidermal hyperplasia.

17. A method of reducing the proliferation of a keratinocyte cell, comprising exposing said cell to a compound of claim 1 to reduce proliferation of said keratinocyte cell.

* * * * *